United States Patent
Chun et al.

(10) Patent No.: US 9,868,980 B2
(45) Date of Patent: *Jan. 16, 2018

(54) DETECTION OF TARGET NUCLEIC ACID SEQUENCE BY PTO CLEAVAGE AND EXTENSION-DEPENDENT SIGNALING OLIGONUCLEOTIDE HYBRIDIZATION ASSAY

(75) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 201 days.

This patent is subject to a terminal disclaimer.

(21) Appl. No.: 14/374,567

(22) PCT Filed: Jul. 3, 2012

(86) PCT No.: PCT/KR2012/005281
§ 371 (c)(1),
(2), (4) Date: Oct. 21, 2014

(87) PCT Pub. No.: WO2013/115442
PCT Pub. Date: Aug. 8, 2013

(65) Prior Publication Data
US 2015/0072887 A1    Mar. 12, 2015

(30) Foreign Application Priority Data

Feb. 2, 2012   (KR) .................. 10-2012-0010681
Mar. 20, 2012  (KR) .................. 10-2012-0028429

(51) Int. Cl.
*C12Q 1/68* (2006.01)

(52) U.S. Cl.
CPC ......... *C12Q 1/6823* (2013.01); *C12Q 1/6818* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. | |
| 5,538,848 A | 7/1996 | Livak et al. | |
| 5,691,142 A | 11/1997 | Dahlberg et al. | |
| 6,326,145 B1 | 12/2001 | Whitcombe et al. | |
| 6,893,819 B1 | 5/2005 | Sorge | |
| 7,381,532 B2 | 6/2008 | Sorge | |
| 7,422,850 B2* | 9/2008 | Marshall | C12Q 1/6823 435/6.1 |
| 2002/0045738 A1 | 4/2002 | Singh et al. | |
| 2004/0191823 A1 | 9/2004 | Virgos et al. | |
| 2005/0142595 A1 | 6/2005 | Maletta et al. | |
| 2005/0221315 A1 | 10/2005 | Braven et al. | |
| 2006/0110748 A1 | 5/2006 | Sorge | |
| 2006/0246469 A1 | 11/2006 | Sorge | |
| 2007/0099211 A1* | 5/2007 | Aivazachvili | B01L 3/5027 435/5 |
| 2007/0231815 A1 | 10/2007 | Sorge | |
| 2008/0131890 A1 | 6/2008 | Allawi et al. | |
| 2008/0160535 A1 | 7/2008 | Gold et al. | |
| 2008/0193940 A1* | 8/2008 | Aivazachvili | C12Q 1/6823 435/6.18 |
| 2008/0241838 A1* | 10/2008 | Scaboo | C12Q 1/6825 435/6.18 |
| 2009/0305237 A1 | 12/2009 | Cantor et al. | |
| 2010/0041049 A1 | 2/2010 | Smith et al. | |
| 2011/0281266 A1 | 11/2011 | Sergeev et al. | |

FOREIGN PATENT DOCUMENTS

| | | |
|---|---|---|
| EP | 1564306 A2 | 8/2005 |
| EP | 2256216 A1 | 1/2010 |
| JP | 2003334097 | 11/2003 |
| JP | 2004305219 A | 11/2004 |
| KR | 1020090067334 A | 6/2009 |
| WO | 1998023774 | 6/1998 |
| WO | 2005010199 A2 | 2/2005 |
| WO | 2005059548 A1 | 6/2005 |
| WO | 2006004949 A1 | 1/2006 |
| WO | 2006005081 A2 | 1/2006 |
| WO | 2008076948 A1 | 6/2008 |
| WO | 2008094902 A2 | 8/2008 |
| WO | 2008102057 A1 | 8/2008 |
| WO | 2010013017 A1 | 7/2009 |

(Continued)

OTHER PUBLICATIONS

Lyamichev, V., et al. "Polymorphism identification and quantitative detection of genomic DNA by invasive cleavage of oligonucleotide probes"; Nature Biotechnology, vol. 17, Mar. 1999, pp. 292-296.

Lohmann et al. A new enzymatic route for production of long 5'-phosphorylated oligonucleotides using suicide cassettes and rolling circle DNA synthesis. BMC Biotechnology. 2007, vol. 7, No. 49.

Olivier, M.; The Invader® assay of SNP genotyping; Elsevier, Mutation Research, vol. 573, 2005, pp. 103-110.

Roux, P., et al.; Direct Measurement of Multiple mRNAs in Nerve Growth Factor-Induced PC12 Cells Using Electrophoretic Tags to Monitor Biomarkers of Neuronal Differentiation in 96-Well Format; Assay and Drug Development Technologies, vol. 2, No. 6, 2004, pp. 637-646.

Allawi, H., et al.; Quantitation of microRNAs using a modified Invader assay; RNA Society, vol. 10, 2004, pp. 1153-1161.

(Continued)

*Primary Examiner* — Aaron Priest
(74) *Attorney, Agent, or Firm* — Gianna Julian-Arnold; Saul Ewing Arnstein & Lehr LLP

(57) ABSTRACT

The present invention relates to the detection of a target nucleic acid sequence by a PCE-SH (PTO Cleavage and Extension-Dependent Signaling Oligonucleotide Hybridization) assay. The present invention does not use probes to be hybridized with target nucleic acid sequences for providing target signals. Interestingly, the present invention uses probes (signaling oligonucleotides) to be hybridized with the extended strand formed in a target-dependent manner in which the extended strand is synthesized using the CTO artificially selected as templates.

23 Claims, 16 Drawing Sheets

(56) References Cited

FOREIGN PATENT DOCUMENTS

| WO | 2009117327 A2 | 10/2009 |
|----|---------------|---------|
| WO | 2010055134 A1 | 5/2010 |
| WO | 2010128041 A1 | 11/2010 |
| WO | 2011028041 A2 | 3/2011 |
| WO | 2011078441 A1 | 6/2011 |
| WO | 2012096523 A2 | 7/2012 |
| WO | 2012134195 A2 | 10/2012 |
| WO | 2013115442 A1 | 8/2013 |

OTHER PUBLICATIONS

Yuan, Y., et al.; Establishment of a Modified High Resolution Melting Assay Based on Allele-specific-extension to Determine Single Nucleotide Polymorphism; Journal of Capital Medical University, vol. 31, No. 6, Dec. 2010, pp. 742-747 [Abstract].
Virus (Wikipedia.com) (reference cited in U.S. Appl. No. 14/114,253).
How many species of bacteria are there (wisegeek.com) (reference cited in U.S. Appl. No. 14/114,253).
Fungus (Wikipedia.com) (reference cited in U.S. Appl. No. 14/114,253).
Plant (Wikipedia.com) (reference cited in U.S. Appl. No. 14/114,253).
Mammal (Wikipedia.com) (reference cited in U.S. Appl. No. 14/114,253).
Murinae (Wikipedia.com) (reference cited in U.S. Appl. No. 14/114,253).
Fish (Wikipedia.com) (reference cited in U.S. Appl. No. 14/114,253).
List of sequenced bacterial genomes (Wikipedia.com) (reference cited in U.S. Appl. No. 14/114,253).
Hessner et al. Genotyping of Factor V G1691A (Leiden) without the Use of PCR by Invasive Cleavage of Oligonucleotide Probes. Clinical Chemistry. vol. 46, No. 8, pp. 1051-1056.
Lambda Exonuclease from thermofisher.com/order/catalog/product/EN0561 (reference cited in U.S. Appl. No. 14/008,096).
Nurmi, et al., A new label technology for the detection of specific polymerase chain reaction products in a closed tube. Nucleic Acids Research, 28, e280, 2000 (reference cited in U.S. Appl. No. 14/008,096).

* cited by examiner

A. Probing and Tagging Oligonucleotide (PTO)

B. Capturing and Templating Oligonucleotide (CTO)

C. Signaling Oligonucleotide (SO)

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

A. Hybridization

B. Primer extension & Cleavage of PTO

C. Hybridization of PTO fragment to CTO and Extension

D. Hybridization of SO to extended strand & Detection

E. (Optional) Melting analysis

Fig. 10A

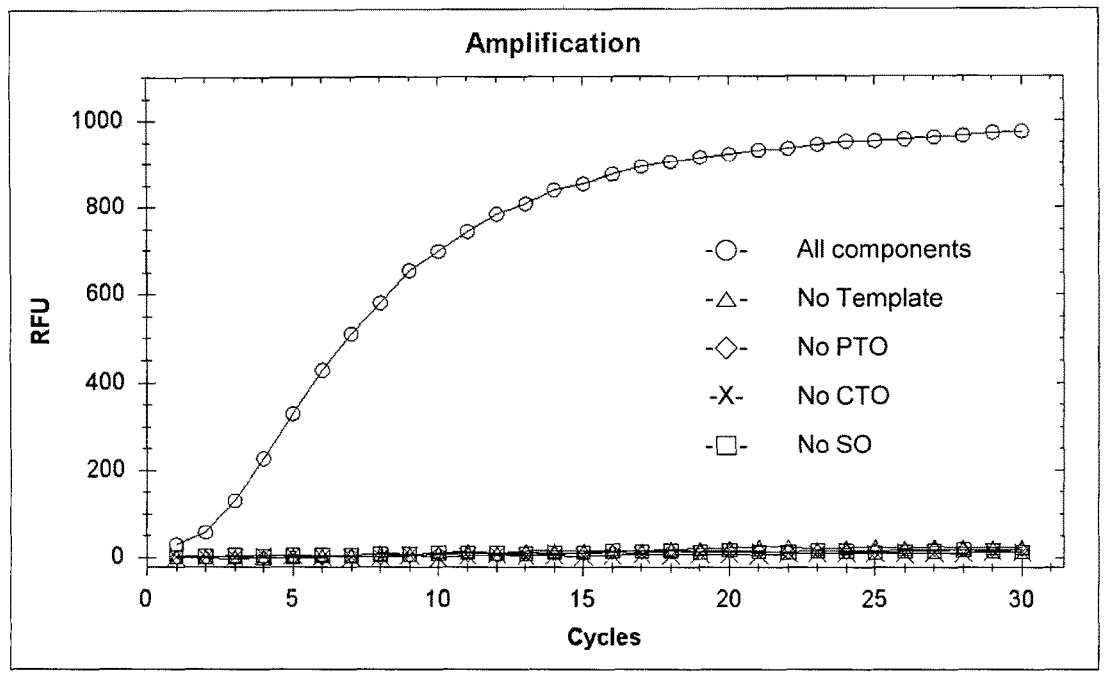

| Template [1] | Upstream Primer | PTO [2] | CTO [3] | SO [4] | Ct |
|---|---|---|---|---|---|
| + | + | + | + | + | 1.72 |
| - | + | + | + | + | - |
| + | + | - | + | + | - |
| + | + | + | - | + | - |
| + | + | + | + | - | - |

[1] Template is a synthetic oligonucleotide for *Neisseria gonorrhoeae* gene.
[2] PTO (Probing and Tagging Oligonucleotide) is blocked with a carbon spacer at its 3'-end.
[3] CTO (Capturing and Templating Oligonucleotide) is blocked with a carbon spacer at its 3'-end.
[4] SO (Signaling Oligonucleotide) has a fluorescent molecule at its 5'-end and a quencher molecule at its 3'-end.

Fig. 10B

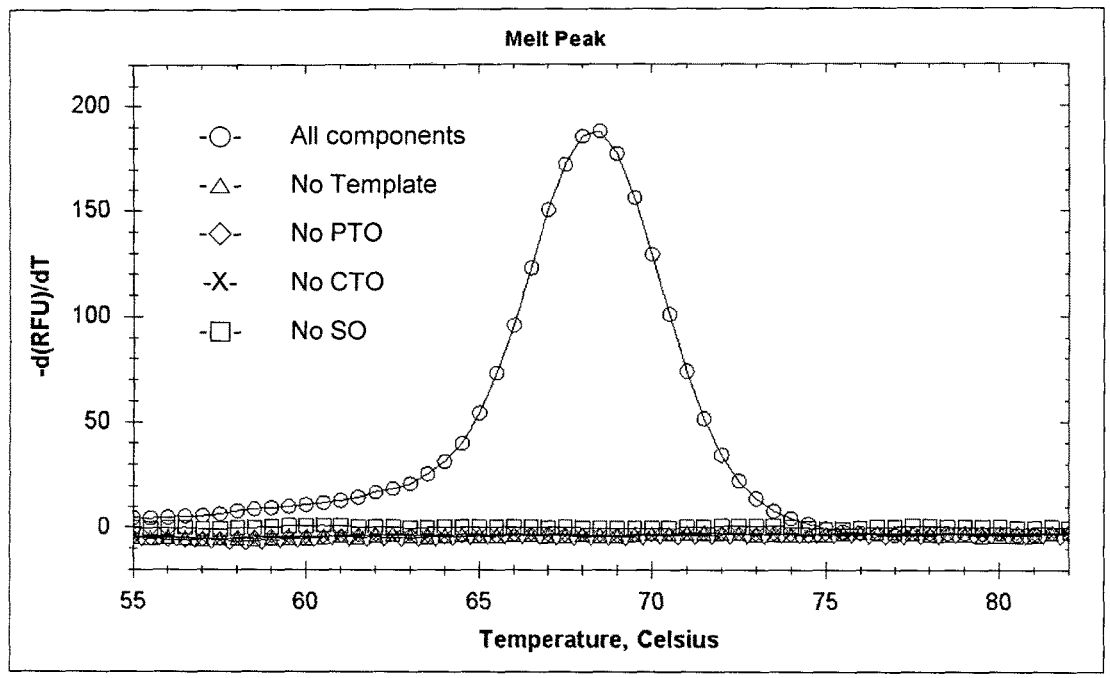

| Template [1] | Upstream Primer | PTO [2] | CTO [3] | SO [4] | Tm [5] |
|---|---|---|---|---|---|
| + | + | + | + | + | 68.5 |
| - | + | + | + | + | - |
| + | + | - | + | + | - |
| + | + | + | - | + | - |
| + | + | + | + | - | - |

[1] Template is a synthetic oligonucleotide for *Neisseria gonorrhoeae* gene.
[2] PTO (Probing and Tagging Oligonucleotide) is blocked with a carbon spacer at its 3'-end.
[3] CTO (Capturing and Templating Oligonucleotide) is blocked with a carbon spacer at its 3'-end.
[4] SO (Signaling Oligonucleotide) has a fluorescent molecule at its 5'-end and a quencher molecule at its 3'-end.
[5] Tm represents melting temperature of the extended strand-SO hybrid.

Fig. 11A

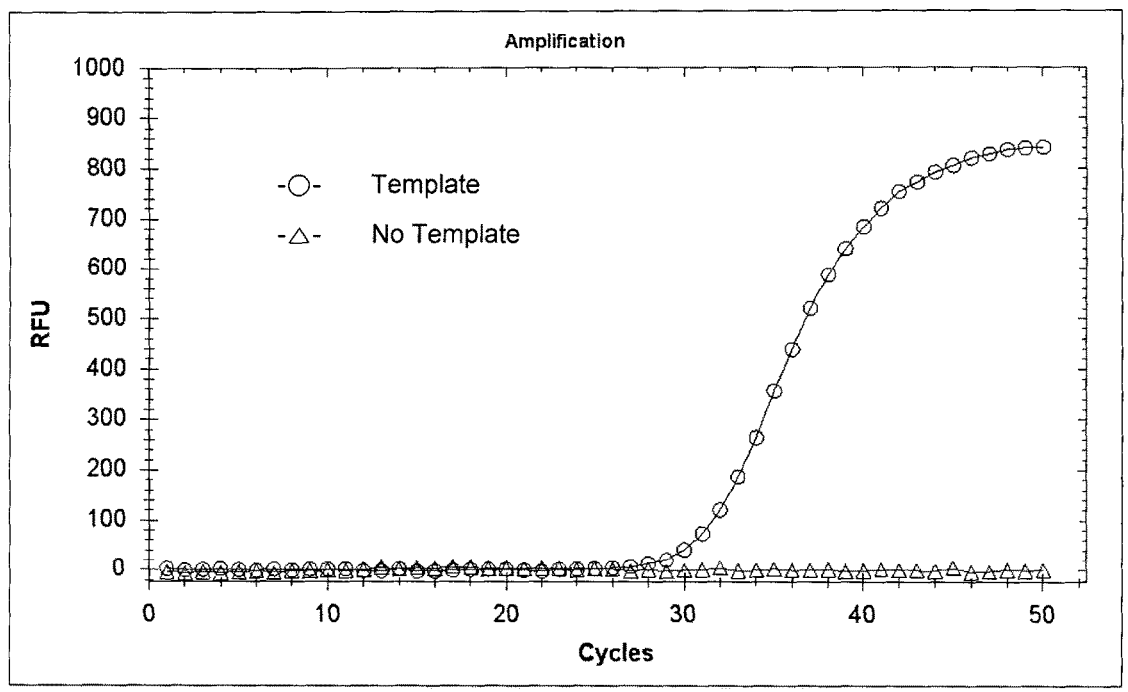

| Template [1] | Primers [2] | PTO [3] | CTO [4] | SO [5] | Ct |
|---|---|---|---|---|---|
| + | + | + | + | + | 30.34 |
| - | + | + | + | + | - |

[1] Template is a genomic DNA of *Neisseria gonorrhoeae*.
[2] Primers are a pair of primers for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3'-end.

Fig. 11B

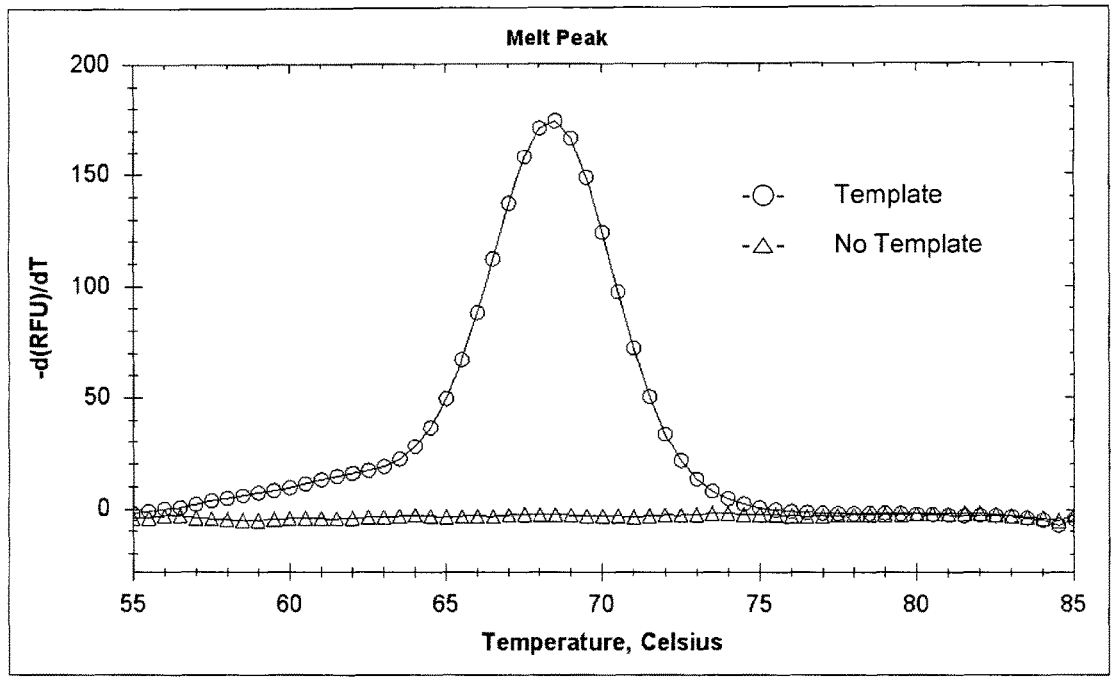

| Template [1] | Primers [2] | PTO [3] | CTO [4] | SO [5] | Tm [6] |
|---|---|---|---|---|---|
| + | + | + | + | + | 68.5 |
| - | + | + | + | + | - |

[1] Template is a genomic DNA of *Neisseria gonorrhoeae*.
[2] Primers are a pair of primers for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] SO (Signaling Oligonucleotide) has a fluorescent molecule at its 5'-end and a quencher molecule at its 3'-end.
[6] Tm represents melting temperature of the extended strand-SO hybrid.

Fig. 12

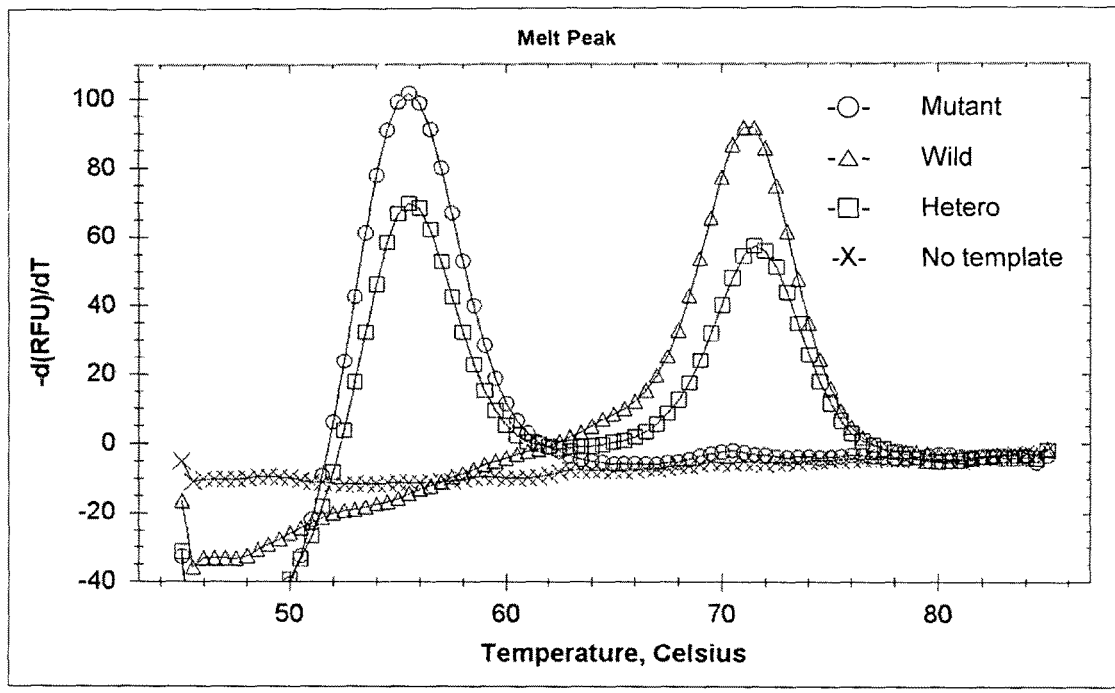

| Template [1] | Primers [2] | PTOs [3] | CTOs [4] | SO [5] | Tm [6] |
|---|---|---|---|---|---|
| Mutant | + | + | + | + | 55.5 |
| Wild | + | + | + | + | 71.0 |
| Hetero | + | + | + | + | 55.5, 71.0 |
| - | + | + | + | + | - |

[1] Template is MTHFR(C677T) wild-type (C), mutant-type (T), or hetero-type (C/T) human genomic DNA.
[2] Primers are a pair of primers for PCR.
[3] PTOs (Probing and Tagging Oligonucleotide) include a PTO for detecting wild-type template and a PTO for mutant-type and are blocked with a carbon spacer at its 3'-end.
[4] CTOs (Capturing and Templating Oligonucleotide) include a CTO for detecting wild-type template and a CTO for mutant-type and are blocked with a carbon spacer at its 3'-end.
[5] SO (Signaling Oligonucleotide) has a quencher molecule at its 5'-end and a fluorescent molecule at its 3'-end.
[6] Tm represents melting temperature of the extended strand-SO hybrid.

Fig. 13A

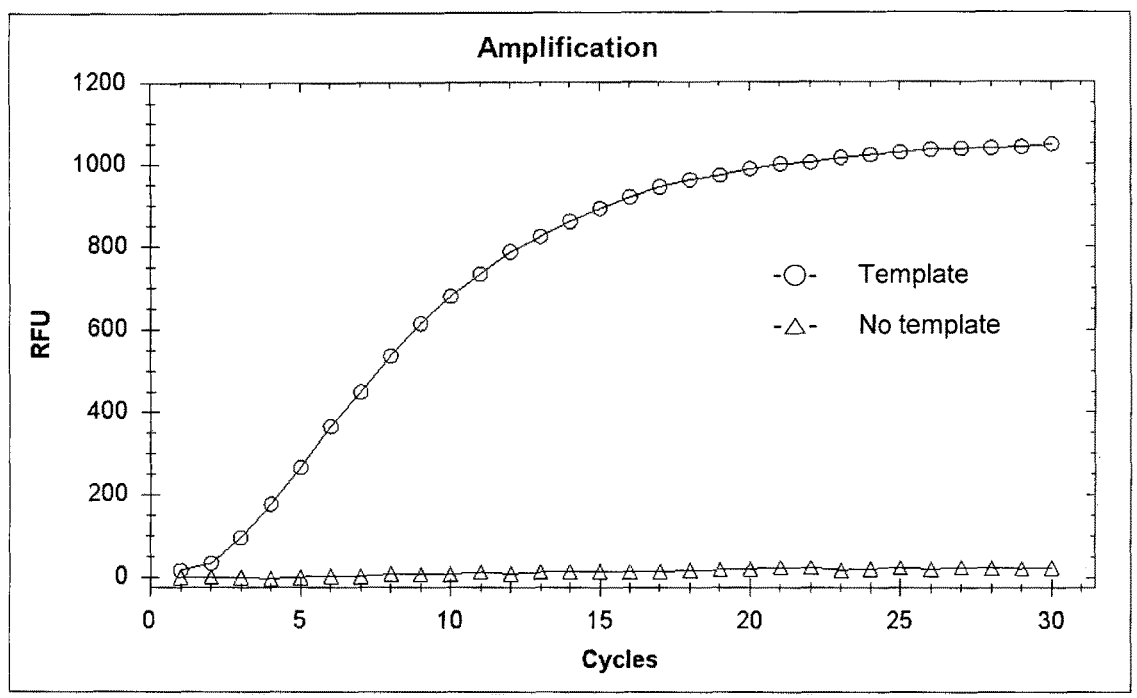

| Template [1] | PTO [2] | CTO [3] | SO [4] | Ct |
|---|---|---|---|---|
| + | + | + | + | 3.10 |
| − | + | + | + | − |

[1] Template is a synthetic oligonucleotide for *Neisseria gonorrhoeae* gene.
[2] PTO (Probing and Tagging Oligonucleotide) is blocked with a carbon spacer at its 3'-end.
[3] CTO (Capturing and Templating Oligonucleotide) is blocked with a carbon spacer at its 3'-end.
[4] SO (Signaling Oligonucleotide) has a fluorescent molecule at its 5'-end and a quencher molecule at its 3'-end.

Fig. 13B

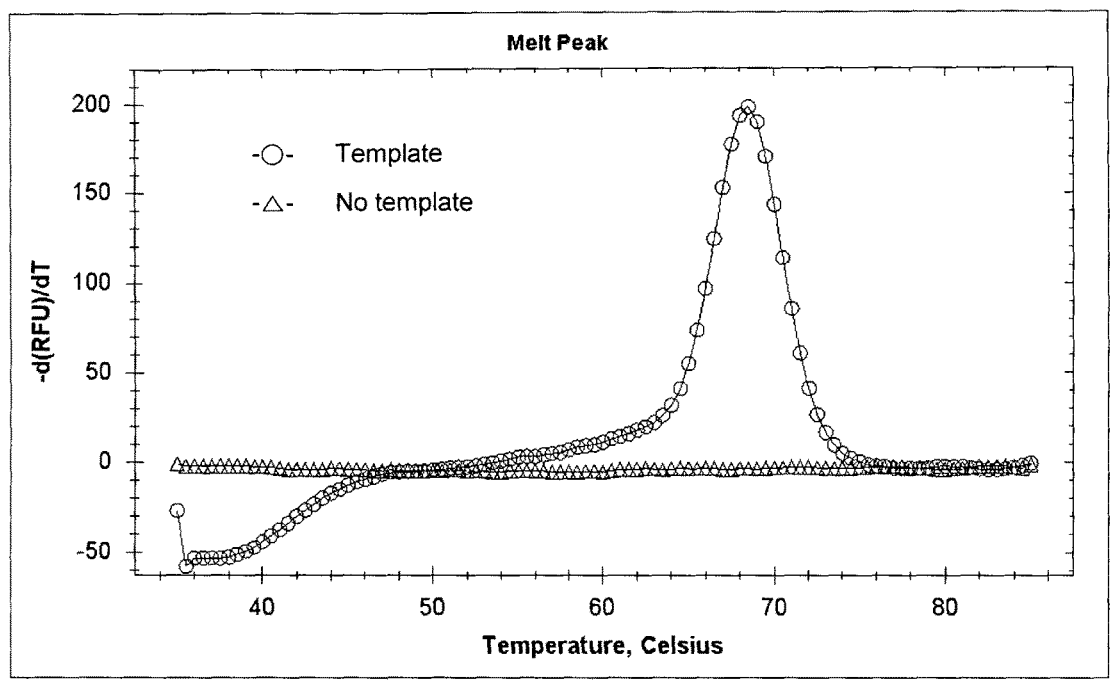

| Template [1] | PTO [2] | CTO [3] | SO [4] | Tm [5] |
|---|---|---|---|---|
| + | + | + | + | 68.5 |
| − | + | + | + | − |

[1] Template is a synthetic oligonucleotide for *Neisseria gonorrhoeae* gene.
[2] PTO (Probing and Tagging Oligonucleotide) is blocked with a carbon spacer at its 3'-end.
[3] CTO (Capturing and Templating Oligonucleotide) is blocked with a carbon spacer at its 3'-end.
[4] SO (Signaling Oligonucleotide) has a fluorescent molecule at its 5'-end and a quencher molecule at its 3'-end.
[5] Tm represents melting temperature of the extended strand-SO hybrid.

DETECTION OF TARGET NUCLEIC ACID SEQUENCE BY PTO CLEAVAGE AND EXTENSION-DEPENDENT SIGNALING OLIGONUCLEOTIDE HYBRIDIZATION ASSAY

CROSS REFERENCE TO RELATED APPLICATIONS

This application claims the priority of PCT/KR2012/005281, filed on Jul. 3, 2012, which claims priority to Korean Patent Application No. 10-2012-0010681, filed Feb. 2, 2012 and Korean Patent Application No. 10-2012-0028429, filed Mar. 20, 2012, the entire contents of each of which are hereby incorporated in total by reference.

SEQUENCE LISTING

This application incorporates by reference the Sequence Listing contained in an ASCII text file named "361406-00020_SeqList.txt" submitted via EFS-Web. The text file was created on Jul. 25, 2014, and is 3 kb in size.

BACKGROUND OF THE INVENTION

Field of the Invention

The present invention relates to the detection of a target nucleic acid sequence by a PCE-SH (PTO Cleavage and Extension-Dependent Signaling Oligonucleotide Hybridization) assay.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

Therefore, there remain long-felt needs in the art to develop novel approaches for detection of a target nucleic acid sequence in a more convenient, reliable and reproducible manner, which is capable of being free from shortcomings of the conventional technologies.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished by enzymatic reactions such as 5' nucleolytic reaction and extension and extension-dependent hybridization as well as probe hybridization. The present protocols are well adopted to liquid phase reactions as well as solid phase reactions, and ensure detection of multiple target sequences with more improved accuracy and convenience.

Accordingly, it is an object of this invention to provide a method for detecting a target nucleic acid sequence from a DNA or a mixture of nucleic acids by a PCE-SH (PTO Cleavage and Extension-Dependent Signaling oligonucleotide Hybridization) assay.

It is another object of this invention to provide a kit for detecting a target nucleic acid sequence from a DNA or a mixture of nucleic acids by a PCE-SH assay.

Other objects and advantages of the present invention will become apparent from the detailed description to follow taken in conjugation with the appended claims and drawings.

BRIEF DESCRIPTION OF THE DRAWINGS

FIG. 10A shows the results of the real-time detection of *Neisseria gonorrhoeae* gene by PCE-SH assay. The SO has a reporter molecule and a quencher molecule.

FIG. 10B shows the results of the detection of *Neisseria gonorrhoeae* gene by PCE-SH assay comprising steps for a melting analysis. The SO has a reporter molecule and a quencher molecule.

FIG. 11A shows the results of the real-time detection of *Neisseria gonorrhoeae* gene by PCE-SH assay with PCR amplification. The SO has a reporter molecule and a quencher molecule.

FIG. 11B shows the results of the detection of *Neisseria gonorrhoeae* gene by PCE-SH assay comprising steps for post-PCR melting analysis. The SO has a reporter molecule and a quencher molecule.

FIG. 12 shows the results of the detection of a single nucleotide variation of a target nucleic acid sequence by PCE-SH assay with comprising steps for post-PCR melting analysis. The C677T mutation on the MTHFR (Methylenetetrahydrofolate reductase) gene was detected.

FIG. 13A shows the results of the real-time detection of *Neisseria gonorrhoeae* gene by PCE-SH assay using upstream oligonucleotide-independent 5' nuclease activity.

FIG. 13B shows the results of the detection of *Neisseria gonorrhoeae* gene by PCE-SH assay comprising steps for a melting analysis using upstream oligonucleotide-independent 5' nuclease activity.

DETAILED DESCRIPTION OF THIS INVENTION

Figure 1:
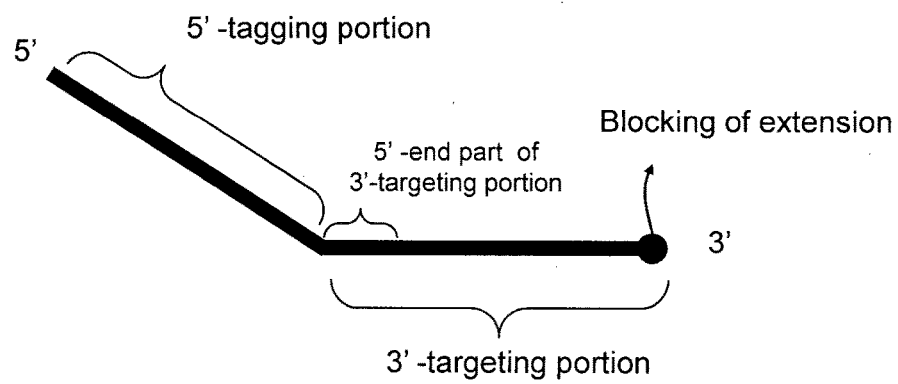
FIG. 1 shows the schematic structures of PTO (Probing and Tagging Oligonucleotide), CTO (Capturing and Templating Oligonucleotide) and SO (Signaling Oligonucleotide) used in a PCE-SH (PTO Cleavage and Extension-Dependent Signaling Oligonucleotide Hybridization) assay. Preferably, the 3'-ends of the PTO, CTO and SO are blocked to prohibit their extension.
Figure 1:
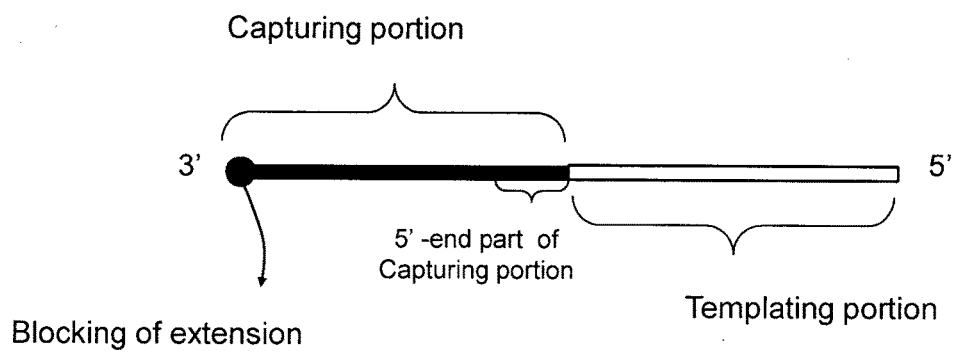
Figure 1:
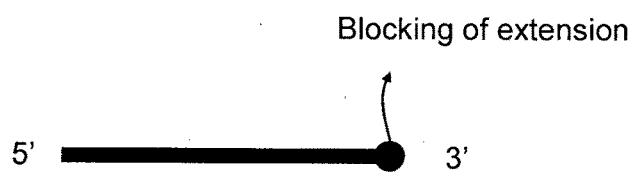

In one aspect of the present invention, there is provided a method for detecting a target nucleic acid sequence from a DNA or a mixture of nucleic acids by a PCE-SH (PTO Cleavage and Extension-Dependent Signaling Oligonucleotide Hybridization) assay, comprising:

(a) hybridizing the target nucleic acid sequence with an upstream oligonucleotide and a probing and targeting oligonucleotide (PTO); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;

(e) hybridizing the extended strand with a signaling oligonucleotide (SO); wherein the SO comprises a complementary sequence to the extended strand and at least one label; the SO provides a detectable signal by hybridization with the extended strand; and (f) detecting the signal; whereby the detection of the signal indicates the presence of the extended strand and the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences, in which target detection is accomplished by enzymatic reactions such as 5' nucleolytic reaction and extension and extension-dependent hybridization as well as probe hybridization. The present protocols are well adopted to liquid phase reactions as well as solid phase reactions, and ensure detection of multiple target sequences with more improved accuracy and convenience.

The present invention employs successive events followed by probe hybridization; cleavage and extension of PTO (Probing and Tagging Oligonucleotide); and extension-dependent signaling oligonucleotide hybridization. Therefore, it is named as a PCE-SH (PTO Cleavage and Extension-Dependent Signaling Oligonucleotide Hybridization) assay.

The PCE-SH assay will be described in more detail as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Preferably, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The 5'-tagging portion of the PTO has a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

For example, the term "non-complementary" in conjunction with the 5'-tagging portion of the PTO means that the 5'-tagging portion is sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1.

Preferably, the hybridization in step (a) is preformed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the templating portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. Preferably, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to a preferred embodiment, the 5'-tagging portion of the PTO not involved in the hybridization with the target nucleic acid sequence forms a single-strand.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to a preferred embodiment, the upstream oligonucleotide is located distantly to the PTO sufficient to induce the PTO cleavage in an extension-dependent manner.

According to a preferred embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. Preferably, the overlapped sequence is 1-10 nucleotides, more preferably 1-5 nucleotides, still more preferably 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to a preferred embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to a preferred embodiment, the method is performed in the presence of a downstream primer. The downstream primer generates additionally a target nucleic acid sequence to be hybridized with the PTO, enhancing sensitivity in a target detection.

According to a preferred embodiment, when the upstream primer and the downstream primer are used, a template-dependent nucleic acid polymerase is additionally employed for extension of the primers.

According to a preferred embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35: 6e40 (2007)).

According to a preferred embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041)

Step (b): Release of a Fragment from the PTO

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, MgCl$_2$ and temperature.

Figure 2:
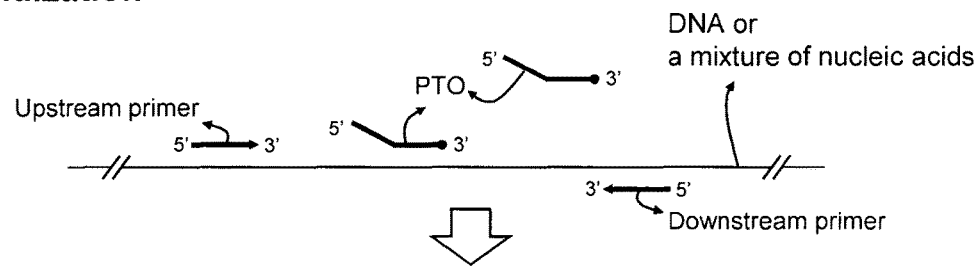
FIG. 2 represents schematically PCE-SH assay using an intrastrand interactive dual label. The SO has a reporter molecule and a quencher molecule.
Figure 2:
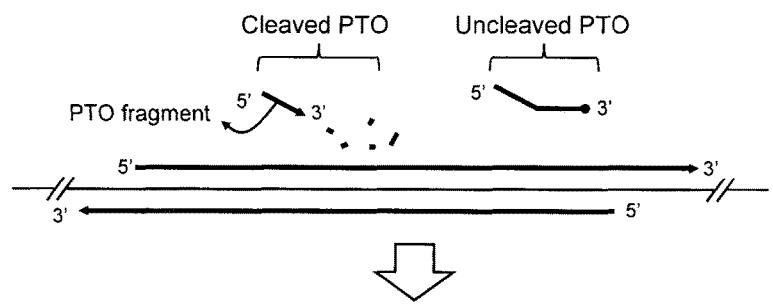
Figure 2:
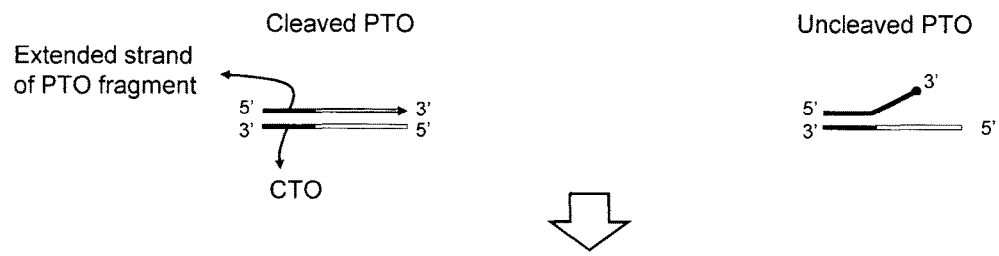
Figure 2:
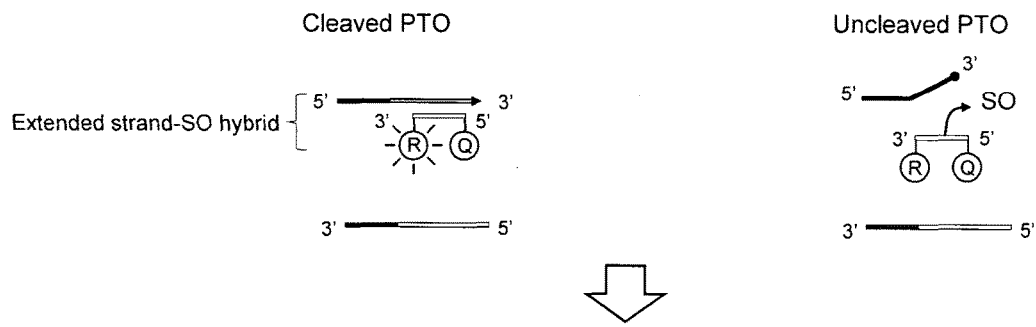

When the PTO is hybridized with the target nucleic acid sequence, its 3'-targeting portion is involved in the hybridization and the 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to a preferred embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "PTO fragment".

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, preferably 1, 2, 3 or 4 nucleotides.

According to a preferred embodiment, the enzyme having the 5' nuclease activity is DNA polymerase having a 5' nuclease activity or FEN nuclease, more preferably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophllus* (Tth), *Thermus filiformis, Thermis flavus, Thermococcus Thermus antranikianil, Thermus caldophilus, Thermus chliarophllus, Thermus flavus, Thermus igniterrae, Thermus lacteus, Thermus oshimai, Thermus ruber; Thermus rubens, Thermus scotoductus, Thermus silvans, Thermus species Z05, Thermus species sps 17, Thermus thermophllus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifex pyrophilus* and *Aquifex aeolieus*. Most preferably, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zllllgii, Methanopyrus kandlen; Methanococcus igneus, Pyrococcus horikoshii, Aeropyrum pernix*, and *Archaeaglobus veneficus*.

Where the upstream primer is used in the step (a), it is preferable that the conditions for cleavage of the PTO comprise extension reaction of the upstream primer.

According to a preferred embodiment, the upstream primer is used in the step (a), a template-dependent polymerase is used for extension of the upstream primer. The template-dependent polymerase may be identical to or different from the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization of the Fragment Released from the PTO with CTO

The fragment released from the PTO is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, it is preferred that the capturing portion of the CTO is designed to comprise a nucleotide sequence complementary to the 5'-tagging portion. When the fragment having the 5'-tagging portion and a 5'-end part of the 3'-targeting portion is released, it is preferred that the capturing portion of the CTO is designed to comprise a nucleotide sequence complementary to the 5'-tagging portion and the 5'-end part of the 3'-targeting portion. When the fragment having a part of the 5'-tagging portion of the PTO is released, it is preferred that the capturing portion of the CTO is designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO may be designed to have a nucleotide sequence complementary to the cleaved 5'-end part of the 3'-targeting portion, overcoming problems associated with mismatch nucleotides (see FIG. 1).

Preferably, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. It is preferable that the nucleotide sequence of the 5'-end part of the capturing portion of the CTO complementary to the cleaved 5'-end part of the 3'-targeting portion is 1-10 nucleotides, more preferably 1-5 nucleotides, still more preferably 1-3 nucleotides.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Preferably, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO is hybridized with the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the Fragment

The extension reaction is carried out using the resultant of the step (c) and a template-dependent nucleic acid polymerase. The fragment hybridized with the capturing portion of the CTO is extended to form an extended strand comprising an extended sequence complementary to the templating portion of the CTO, thereby forming an extended duplex. In contrast, uncleaved PTO hybridized with the capturing portion of the CTO is not extended such that no extended strand is formed.

The term used herein "extended duplex" means a duplex formed by extension reaction in which the fragment hybridized with the capturing portion of the CTO is extended using the templating portion of the CTO as a template and the template-dependent nucleic acid polymerase.

The term used herein "extended strand" in conjunction with the fragment means a sequence composed of the fragment and its extended sequence.

The term used herein "extended sequence" in conjunction with the fragment means only a newly extended sequence which is a portion of the extended strand except the fragment.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase. Preferably, the polymerase is a thermostable DNA polymerase which may be obtained from a variety of bacterial species, including *Thermus aquaticus* (Taq), *Thermus thermophllus* (Tth), *Thermus filiformis*, *Thermis flavus*, *Thermococcus literalis*, *Thermus antranikianii*, *Thermus caldophllus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritime*, *Thermotoga neapolitana*, *Thermosiphoafricanus*, *Pyrococcus furiosus* (Pfu), *Pyrococcus woesei*; *Pyrococcus horikoshii*, *Pyrococcus abyssi*, *Pyrodictium occultum*, *Aquifex pyrophllus* and *Aquifex aeolieus*. Most preferably, the template-dependent nucleic acid polymerase is Taq polymerase.

According to a preferred embodiment, the template-dependent nucleic acid polymerase includes a reverse transcriptase.

According to a preferred embodiment, the enzyme having the 5' nuclease activity used in the step (b) is identical to the template-dependent nucleic acid polymerase used in the step (d). More preferably, the enzyme having the 5' nuclease activity used in the step (b), the template-dependent nucleic acid polymerase used for extension of the upstream primer and the template-dependent nucleic acid polymerase used in the step (d) are identical to one another.

Step (e): Signal Generation by Hybridization Between the Extended Strand and SO

Following the extension reaction, the extended strand is hybridized with a signaling oligonucleotide (SO). The signal indicative of the presence of the target nucleic acid sequence is provided. The signal includes a signal generation or extinguishment, or signal change (signal increase or decrease).

Figure 6:
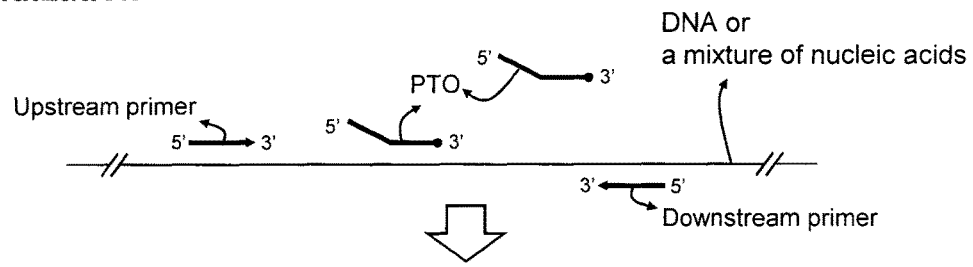
FIG. 6 represents schematically PCE-SH assay using an interstrand interactive dual label. The SO comprises a reporter molecule and the extended strand comprises quencher-iso-dG residue incorporated during the extension reaction.
Figure 6:
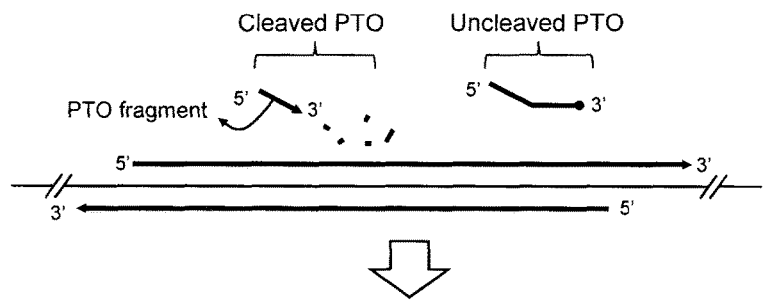
Figure 6:
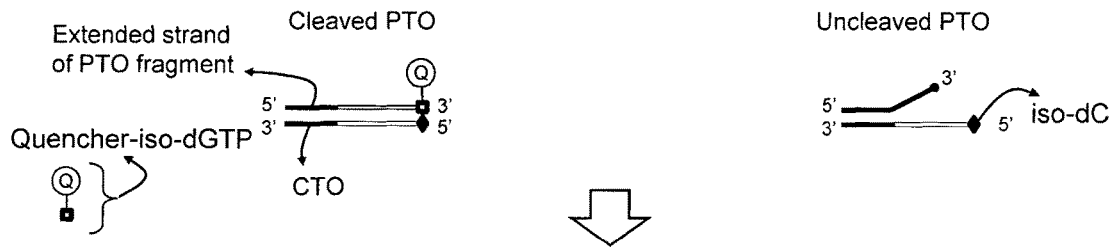
Figure 6:
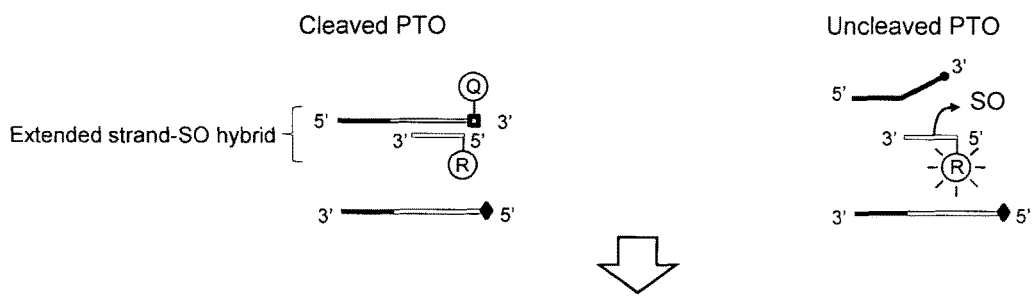

The SO to be hybridized with the extended strand comprises a complementary sequence to the extended strand.

Where the SO comprises a complementary sequence only to the PTO fragment, a non-target signal may not be generated due to hybridization of undigested PTO and the SO in some of signaling systems described hereinbelow.

Where the position of incorporated labels in the extended strand as illustrated in FIG. 6 is suitably adjusted, a non-target signal may not be generated even using the SO comprising a complementary sequence only to the PTO fragment.

In the meantime, where the SO comprises a complementary sequence only to the PTO fragment, a non-target signal may be generated due to hybridization of undigested PTO and the SO in some of signaling systems described hereinbelow (e.g., the signaling system of FIG. 2).

Where the non-target signal becomes problematic, a portion of the SO should be designed to comprise a complementary sequence to a portion of the extended sequence newly synthesized.

According to a preferred embodiment, the SO comprises a complementary sequence to the extended sequence.

According to a preferred embodiment, at least a portion of the SO comprises a complementary sequence to the extended sequence. The portion of the SO comprising a complementary sequence to the extended sequence is at least one, two, three, four, five or ten nucleotides in length.

When a portion of the SO is designed to comprise a complementary sequence to a portion of the extended sequence newly synthesized, the $T_m$ value of the hybridization resultant of the SO and the extended strand becomes different from that of the hybridization resultant of the SO and the undigested PTO. The difference in the $T_m$ values ensures to differentiate signals from the two hybridization resultants. For example, non-target signals may be excluded in a real-time detection by adjusting temperature for detection in considering $T_m$ values, or in a melting curve analysis by melting peaks.

Preferably, the SO may comprise throughout its whole sequence a complementary sequence to the extended sequence. Alternatively, the SO may comprise a portion having a complementary sequence to the extended sequence. For instance, one portion of the SO may comprise a complementary sequence to the extended sequence and the other portion may comprise a complementary sequence to the fragment.

Preferably, the SO comprises throughout its whole sequence a complementary sequence to the extended sequence.

The SO may have any length, for example, 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30, nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides.

The SO may have a hairpin structure.

Preferably, the 3'-end of the SO is blocked to prohibit its extension.

Alternatively, the SO having a non-blocked 3'-OH end may be extended.

The signaling system adopted in the present invention is featured by association of signal generation with hybridization of the SO. In other words, upon hybridization of the SO with the extended strand, a detectable signal is provided. The hybridization of the SO with the extended strand occurs only when the target nucleic acid sequence is present and the PTO is cleaved. Therefore, the detectable signal is indicative of the presence of the target nucleic acid sequence. In this regard, if desired, the present invention may be carried out in a real-time manner.

To directly associate the hybridization of the SO with signals, the present invention uses at least one label linked to the SO.

According to a preferred embodiment, the detectable signal indicative of the presence of the target nucleic acid sequence is provided by (i) the label linked to the SO, (ii) a combination of the label linked to the SO and a label linked to the fragment from the PTO, (iii) a combination of the label linked to the SO and a label to be incorporated into the extended strand during the extension reaction of the step (d), or (iv) a combination of the label linked to the SO and an intercalating dye.

The labeling systems useful in this invention will be described in detail as follows:

(i) Single Label Linked to the SO

Figure 3:
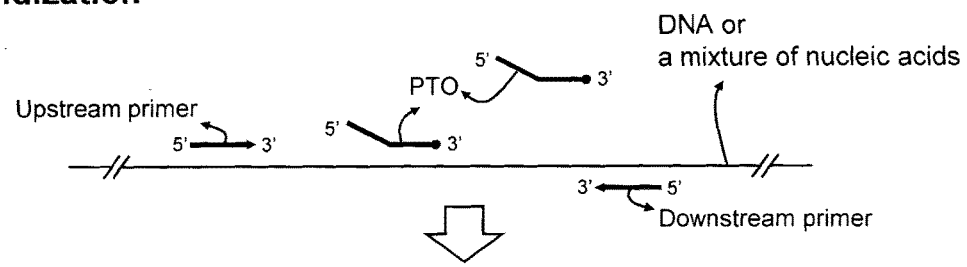
FIG. 3 represents schematically PCE-SH assay using a single label. The SO has a reporter molecule as a single label. The reporter molecule is required to show different signal intensity depending on its presence on a single-stranded form or a double-stranded form.
Figure 3:
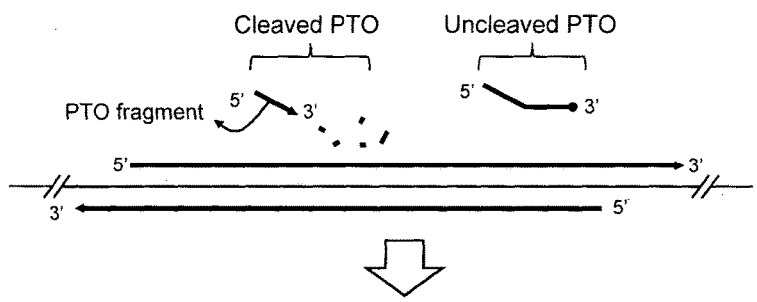
Figure 3:
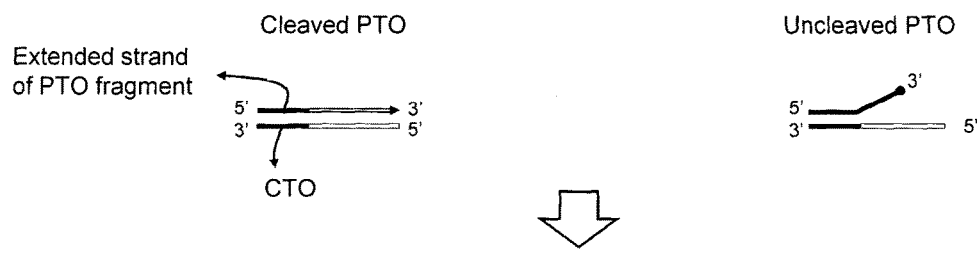
Figure 3:
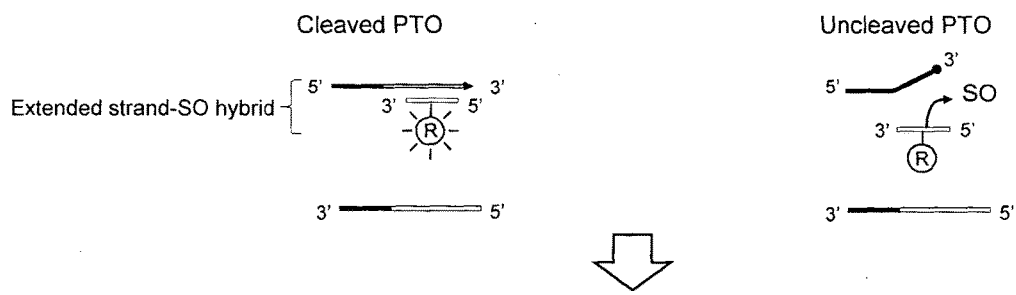

The present invention may provide signal for formation of the extended strand indicating the presence of the target nucleic acid sequence using a single label (see FIG. 3).

According to a preferred embodiment, the SO is labeled with a single label and the hybridization between the SO and the extended strand in the step (e) induces change in signal from the single label to provide the detectable signal.

The single label used herein has to be capable of providing a different signal depending on its presence on a double strand or single strand. The single label includes a fluorescent label, a luminescent label, a chemiluminescent label, an electrochemical label and a metal label.

Preferably, the single label includes a fluorescent label which provides different-intensity signals depending on whether it is linked to a double-stranded or single-strand nucleic acid.

FIG. 3 illustrates a preferable embodiment of the present invention using a single label. As illustrated in FIG. 3, the single fluorescent label linked to the SO hybridized with the extended strand exhibits more intense fluorescence that that linked to the SO not hybridized.

The changes (increase or decrease) in fluorescent intensity of single fluorescent labels are measured to detect the presence of the target nucleic acid sequence.

The types and preferable binding sites of single fluorescent labels used in this invention are disclosed U.S. Pat. Nos. 7,537,886 and 7,348,141, the teachings of which are incorporated herein by reference in their entity. Preferably, the single fluorescent label includes JOE, FAM, TAMRA, ROX and fluorescein-based label. The labeled nucleotide residue is preferably positioned at internal nucleotide residue within the oligonucleotide rather than at the 5'-end or the 3'-end.

According to a preferred embodiment, the single label on the SO is located at 1-15 nucleotide, 1-10 nucleotide or 1-5 nucleotide apart from its 5'-end or its 3'-end. More preferably, the single label is located at the middle portion of SO.

The single fluorescent label useful in the present invention may be described with reference to descriptions for reporter and quencher molecules as indicated below.

(ii) Intrastrand Interactive-Dual Label Linked to SO

The interactive label system is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively.

Preferably, the signal indicative of the formation of the extended strand (i.e., the presence of the target nucleic acid sequence) is generated by interactive label systems, more preferably the FRET label system (i.e., interactive dual label system).

According to a preferred embodiment, the SO is labeled with an interactive dual label comprising a reporter molecule and a quencher molecule and the hybridization between the SO and the extended strand in the step (e) induces change in signal from the interactive dual label to provide the detectable signal. Prior to hybridization of the SO, the reporter molecule and the quencher molecule on the SO are conformationally adjacent to each other to allow the quencher molecule to quench the signal from the reporter molecule. Upon hybridization, the reporter molecule and the quencher molecule on the SO are conformationally separated to allow the quencher molecule to unquench the signal from the reporter molecule, causing changes in signals from the interactive dual label.

FIG. 2 represents a preferable embodiment of the present invention using an interactive dual label. The fragment released from the PTO hybridized with the target nucleic acid sequence is hybridized with the capturing portion of the CTO and extended to form the extended strand. Upon hybridization of the extended strand with the SO, the reporter molecule and the quencher molecule on the SO are conformationally separated to allow the quencher molecule to unquench the signal from the reporter molecule, giving rise to changes in signals from the interactive dual label (e.g., increase in signal from reporter molecules). In contrast, where the target nucleic acid sequence is not present, the cleavage of the PTO does not occur. The undigested PTO is not extended while it is hybridized with the capturing portion of the CTO. The reporter molecule and the quencher molecule on the SO not involved in the hybridization are conformationally adjacent to each other to allow the quencher molecule to quench the signal from the reporter molecule.

The expression used herein "the reporter molecule and the quencher molecule are conformationally adjacent" means that the reporter molecule and the quencher molecule are three-dimensionally adjacent to each other by a conformational structure of the fragment or SO such as random coil and hairpin structure.

The expression used herein "the reporter molecule and the quencher molecule are conformationally separated" means that the reporter molecule and the quencher molecule are three-dimensionally separated by change of a conformational structure of the SO upon the formation of a double strand by hybridization with the extended strand.

According to a preferred embodiment, the reporter molecule and the quencher molecule are positioned at the 5'-end (or 3'-end) and 3'-end (or 5'-end) of the SO. According to a preferred embodiment, one of the reporter molecule and the quencher molecule on the SO is located at its 5'-end or at 1-5 nucleotides apart from its 5'-end and the other is located to quench and unquench the signal from the reporter molecule depending on conformation of SO According to the preferred embodiment, one of the reporter molecule and the quencher molecule on the SO is located at its 3'-end or at 1-5 nucleotides apart from its 3'-end and the other is located to quench and unquench the signal from the reporter molecule depending on conformation of the SO.

According to a preferred embodiment, the reporter molecule and the quencher molecule are positioned at no more than 80 nucleotides, more preferably no more than 60 nucleotides, still more preferably no more than 30 nucleotides, still much more preferably no more than 25 nucleotides apart from each other. According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO'-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule (or dark quencher molecule) capable of quenching a fluorescence of a wide range of wavelengths or a specific wavelength may be used in the present invention. Examples of those are BHQ and DABCYL.

In the FRET label adopted to the SO, the reporter encompasses a donor of FRET and the quencher encompasses the other partner (acceptor) of FRET. For example, a fluorescein dye is used as the reporter and a rhodamine dye as the quencher.

(iii) Interstrand Interactive-Dual Label

In the embodiment using the interstrand interactive-dual label, the extended strand has one of an interactive dual label comprising a reporter molecule and a quencher molecule and the SO has the other of the interactive dual label.

Figure 5:
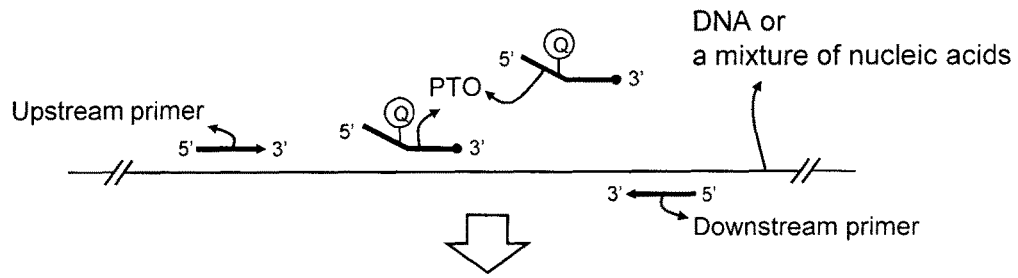
FIG. 5 represents schematically PCE-SH assay using an interstrand interactive dual label. The SO comprises a reporter molecule and the extended strand comprises a quencher molecule.
Figure 5:
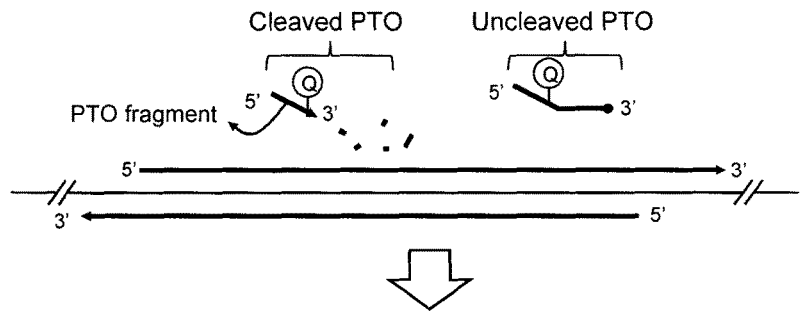
Figure 5:
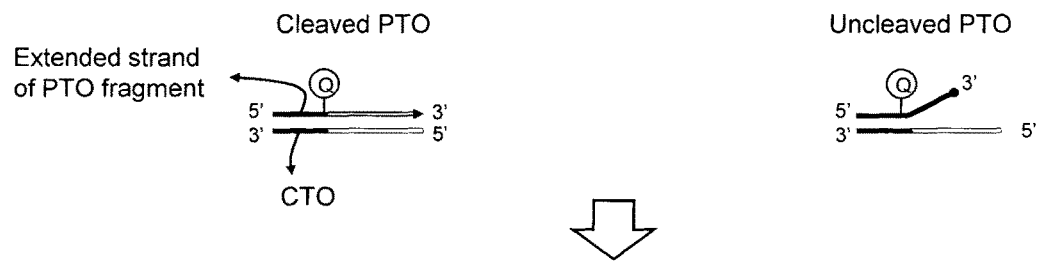
Figure 5:
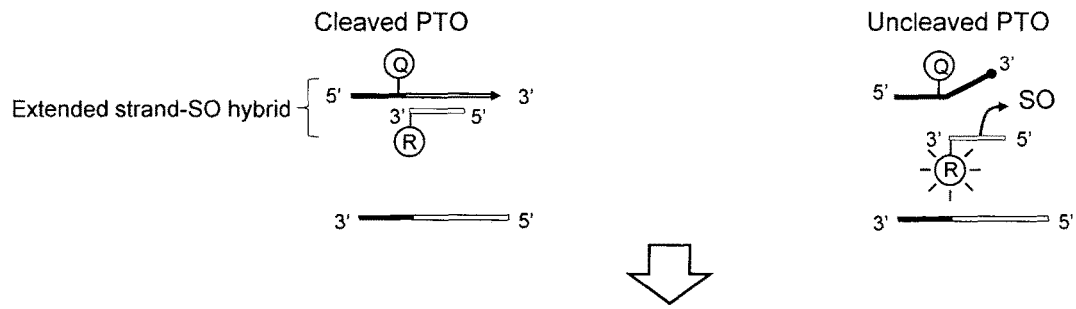

The embodiment using the interstrand interactive-dual label may be conducted in accordance with the following three fashions:

According to the first fashion, the SO comprises one label among a reporter molecule and a quencher molecule of an interactive dual label, the fragment from the PTO comprises the other label among the reporter molecule and the quencher molecule; the extended strand comprises the label originated from the fragment from the PTO, and wherein the hybridization between the SO and the extended strand induces change in signal from the interactive dual label to provide the detectable signal (see FIG. 5).

A label linked to the SO may be either a reporter molecule or a quencher molecule, and a label to the fragment may be either a quencher molecule or a reporter molecule.

The labeling site on the PTO is determined in considering its cleavage site, so that the PTO fragment may have the label.

The label may be linked to any site (e.g., the tagging portion of the PTO) on the PTO fragment, so long as it interacts with the label to the SO upon hybridization with the SO to induce change in signals. The label may be linked to any site (e.g., the 5'-end of the SO) on the SO, so long as it interacts with the label on the PTO fragment upon hybridization with the PTO fragment to induce change in signals.

According to the second fashion, the SO comprises one label among a reporter molecule and a quencher molecule of an interactive dual label, and the templating portion of the CTO comprises a nucleotide having a first non-natural base; wherein the extension reaction in the step (d) is performed in the presence of a nucleotide having both a second non-natural base with a specific binding affinity to the first non-natural base and the other among the reporter molecule and the quencher molecule, thereby incorporating the label into the extended strand; wherein the hybridization between the SO and the extended strand induces change in signal from the interactive dual label to provide the detectable signal (see FIG. 6).

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner.

Specific examples of non-natural bases include the following bases in base pair combinations: iso-C/iso-G, iso-dC/iso-dG, K/X, H/J, and M/N (see U.S. Pat. No. 7,422,850).

The label incorporated during the extension is preferably linked to a nucleotide, more preferably to a nucleoside triphosphate. Preferably, the label is bound to a base of a nucleoside triphosphate.

The exemplified embodiment is described with reference to FIG. 6. The fragment is hybridized with the CTO with a nucleotide having a non-natural base (e.g., iso-dC) with a specific binding affinity to a non-natural base (e.g., iso-dG). The extension is carried out in the presence of a nucleotide having the iso-dG labeled with a quencher to form the extended strand. In the extension reaction, the nucleotide having iso-dG with a quencher is incorporated at an opposition site to the nucleotide having iso-dC. Following the hybridization of the extended strand containing the quencher-iso-dG with the SO labeled with a reporter, the quencher on the extended strand quenches signal from the reporter on the SO to induce changes in signal, providing the detectable signal.

One of the interactive dual label is linked to the SO and the other is incorporated into the extended strand from a reaction solution during the extension reaction.

A label linked to the SO may be either a reporter molecule or a quencher molecule, and a label incorporated into the extended strand may be either a quencher molecule or a reporter molecule.

The label incorporated into the extended strand may be linked to any site on the extended strand (e.g., the 3'-end of the extended strand), so long as it interacts with the label to the SO upon hybridization with the SO to induce change in signals. The label may be linked to any site (e.g., the 5'-end of the SO) on the SO, so long as it interacts with the label incorporated into the extended strand upon hybridization with the extended strand to induce change in signals.

Figure 7:
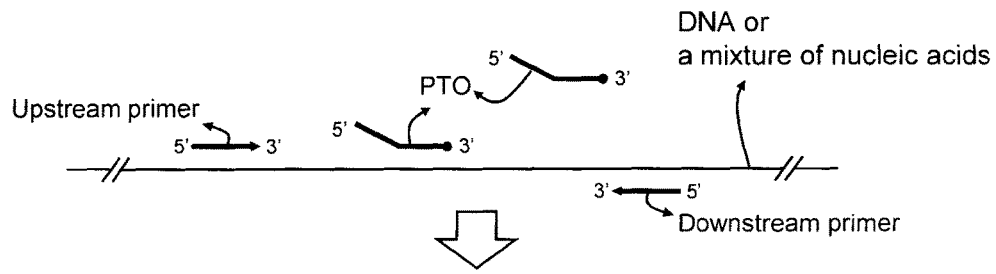
FIG. 7 represents schematically PCE-SH assay using an interstrand interactive dual label. The SO comprises a reporter molecule and the extended strand comprises quencher-dA residues incorporated during the extension reaction.
Figure 7:
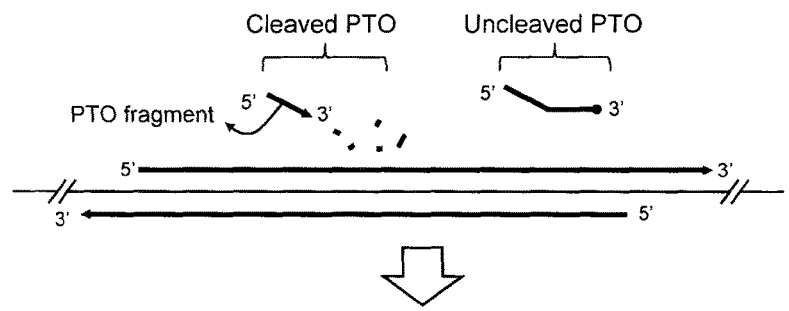
Figure 7:
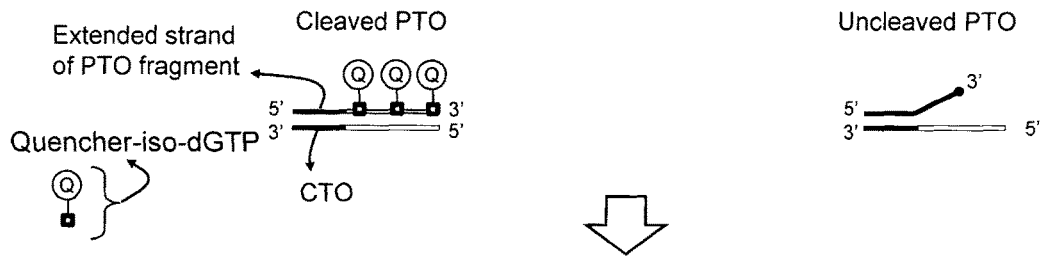
Figure 7:
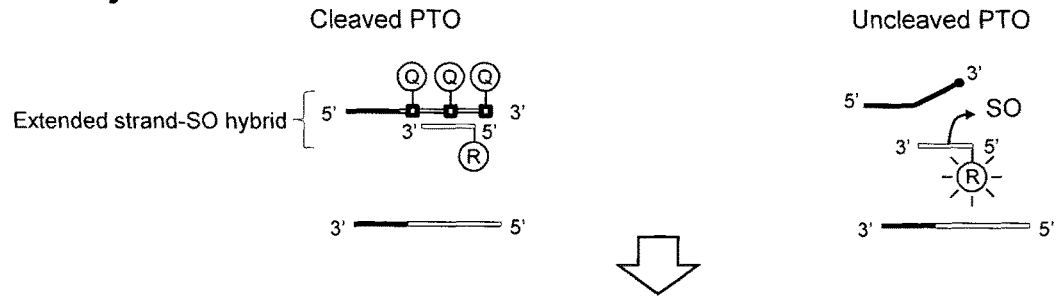

According to the third fashion, the SO comprises one label among a reporter molecule and a quencher molecule of an interactive dual label, and the extension reaction in the step (d) is performed in the presence of a nucleotide having the other among the reporter molecule and the quencher molecule, thereby incorporating the label into the extended strand; wherein the hybridization between the SO and the extended strand induces change in signal from the interactive dual label to provide the detectable signal (see FIG. 7).

A label linked to the SO may be either a reporter molecule or a quencher molecule (preferably reporter molecule), and a label incorporated into the extended strand may be either a quencher molecule or a reporter molecule (preferably quencher molecule).

(iv) Interactive-Dual Label Using Two SOs

Figure 4:
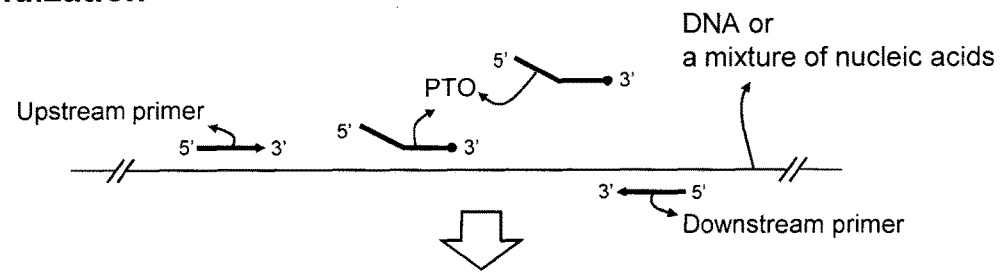
FIG. 4 represents schematically PCE-SH assay using an interstrand interactive dual label and two SOs. The two SOs each comprises one label among a reporter molecule and a quencher molecule of an interactive dual label.
Figure 4:
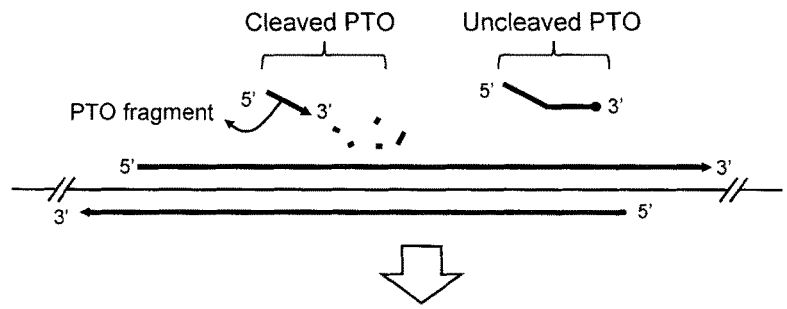
Figure 4:
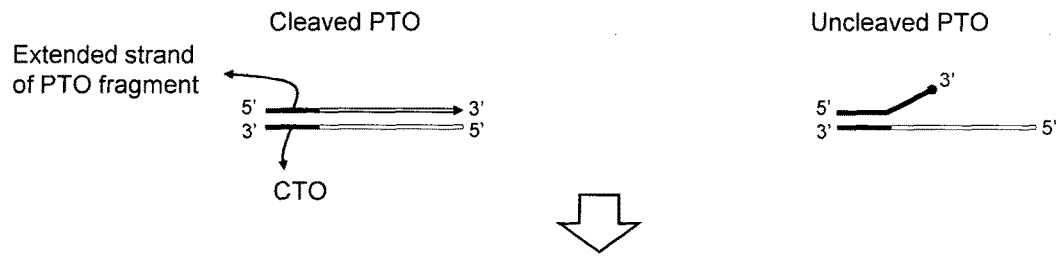
Figure 4:
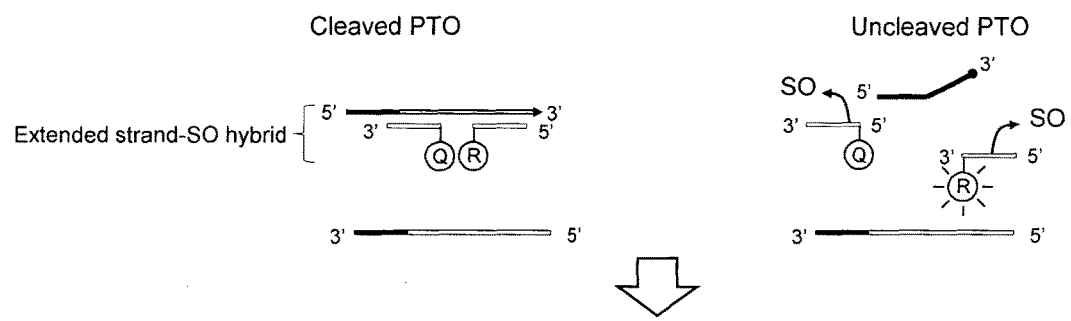

In the embodiment of the interactive-dual label using two SOs, the method of the present invention uses an additional SO comprising a complementary sequence to the extended strand, the two SOs are hybridized with the extended strand in an adjacent manner, the two SOs each comprises one label among a reporter molecule and a quencher molecule of an interactive dual label; and the hybridization between the two SOs and the extended strand induces change in signal from the interactive dual label to provide the detectable signal (see FIG. 4).

Preferably, at least one of the two SOs comprises a portion hybridized to a newly extended sequence in the extension reaction.

The principle underlying the performance of the embodiment of the interactive-dual label using two SOs are as follows: The fragment released from the PTO hybridized with the target nucleic acid sequence is hybridized with the capturing portion of the CTO and extended to form the extended strand. Afterwards, the two SOs are hybridized with the extended strand. In the hybridization, since the two SOs are adjacently hybridized with the extended strand, the reporter molecule and the quencher molecule on the two SOs are adjacent to each other to allow the quencher molecule to quench the signal from the reporter molecule, resulting in change in signals from the interactive dual label (e.g., increase in signal from reporter molecules). In contrast, where the target nucleic acid sequence is not present, the cleavage of the PTO does not occur. The undigested PTO is not extended while it is hybridized with the capturing portion of the CTO. The reporter molecule and the quencher molecule on the two SOs not involved in the hybridization are separated to each other to generate signal from the reporter molecule.

According to a preferred embodiment, the two SOs may be hybridized with any sites of the extended strand so long as their hybridization with the extended strand permits the quencher molecule to quench the signal from the reporter molecule. Preferably, the two SOs are positioned in an immediately adjacent manner or 1-5 nucleotides apart from each other.

According to a preferred embodiment, where the two SOs may be adjacently hybridized with the extended strand, the reporter molecule and the quencher molecule may be linked to any sites of the two SOs so long as the quencher molecule quenches the signal from the reporter molecule. For example, the reporter molecule or the quencher molecule is linked to the 5'-end of one SO or 1-5 nucleotides apart from its 5'-end, and the quencher molecule or the reporter molecule to the 3'-end of the other SO or 1-5 nucleotides apart from its 3'-end.

(v) FRET Label Using Intercalating Dyes

According to the present invention, a FRET (fluorescence resonance energy transfer) signaling becomes practical using intercalating dyes.

Figure 8:
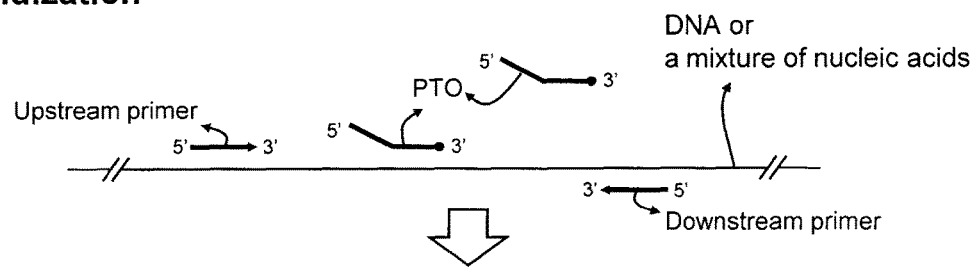
FIG. 8 represents schematically PCE-SH assay using intercalating dyes. The SO comprises an acceptor. SYBR green is used as donors.
Figure 8:
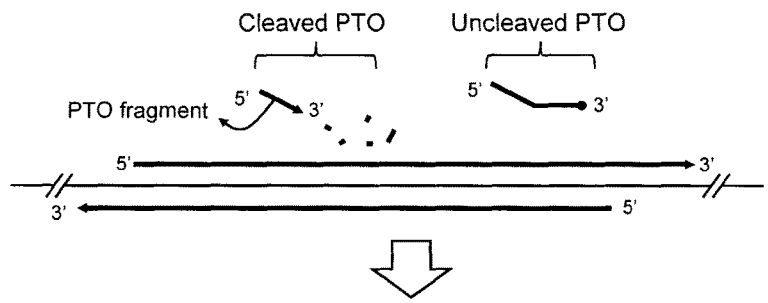
Figure 8:
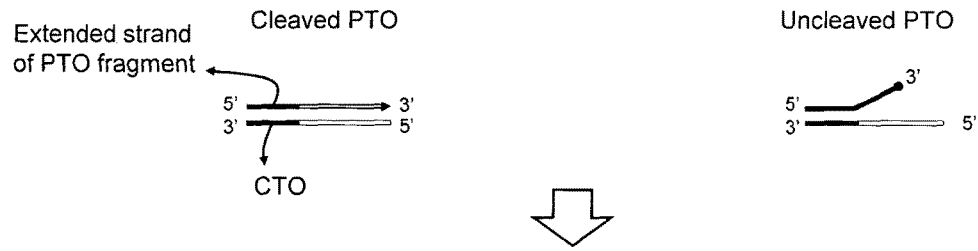
Figure 8:
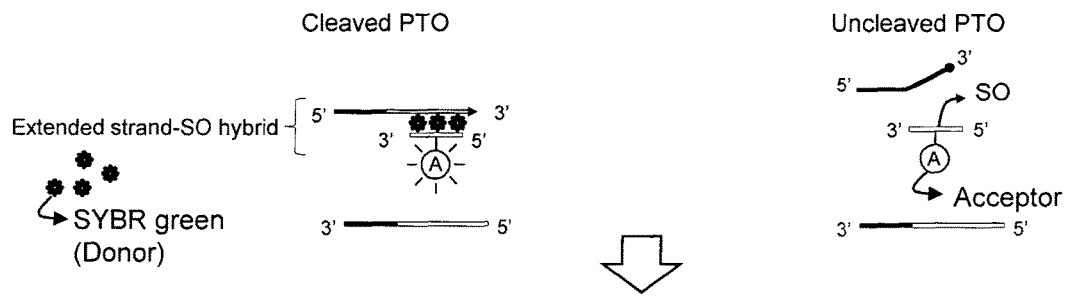

According to a preferred embodiment, the SO comprises an acceptor of a FRET and the hybridization in the step (e) is preformed in the presence of an intercalating dye; wherein the hybridization between the SO and the extended strand induces change in signal from the acceptor of the SO to provide the detectable signal (see FIG. 8).

Exemplified intercalating dyes useful in this invention include SYBR™ Green I, PO-PRO™-1, BO-PRO™-1, SYTO™43, SYTO™44, SYTOX™45, SYTOX™ Blue, POPO™-1, POPO™-3, BOBO™-1, BOBO™-3, LO-PRO™-1, JO-PRO™-1, YO-PRO™1, TO-PRO™1, SYTO™11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

The principle underlying the performance of the embodiment of the FRET label using intercalating dyes are as follows: The fragment released from the PTO hybridized with the target nucleic acid sequence is hybridized with the capturing portion of the CTO and extended to form the extended strand. Afterwards, the SO labeled with the acceptor is hybridized with the extended strand to form a double-stranded nucleic acid molecule and then the intercalating dyes are bound to the double-stranded nucleic acid molecule. The energy transfer occurs from the intercalating dyes serving as a donor molecule to the acceptor by illumination for donor excitation and induces change in signal from the acceptor to provide the detectable signal. In contrast, the FRET phenomenon does not occur in the absence of the target nucleic acid sequence, resulting in no signal change.

According to a preferred embodiment, the acceptor linked to the SO includes various single fluorescent labels described above, but not limited to.

A label may be linked to the SO or the PTO by conventional methods. Preferably, it is linked to the SO or PTO through a spacer containing at least three carbon atoms (e.g., 3-carbon spacer, 6-carbon spacer or 12-carbon spacer).

The SO useful in the present invention includes any probes capable of providing signals dependent on hybridization, for example, Molecular Beacon™ (U.S. Pat. No. 5,925,517), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), LUX™ (I. A. Nazarenko, et al. Nucleic Acids Res 2002, 30:2089-2095, and U.S. Pat. No. 7,537,886) and Hybridization probe (Bernard P S, et al., Clin Chem 2000, 46, 147-148 and Deepti Parashar et al., Indian J Med Res 124, review article October 2006 385-398).

Step (f): Detection of Target Signal

Finally, the detectable signal provided in the step (e) is detected, whereby the detection of the signal indicates the presence of the extended strand and the presence of the target nucleic acid sequence.

As discussed above, the hybridization event of the SO is synchronized with the signaling event from labels of the hybridization resultant to provide signals indicative of the target nucleic acid sequence. In this regard, the present invention may be carried out in a real-time manner using labels proving signals detectable in a real-time fashion.

Alternatively, the detection of the target signal may be carried out by a melting analysis because the labels used in the present invention are capable of providing detectable signals during melting of the hybridization resultant or melting and hybridization of the hybridization resultant.

The term used herein "melting analysis" means a method in which a target signal indicative of the presence of the extended duplex is obtained by melting of the extended duplex, including a method to measure signals at two different temperatures, melting curve analysis, melting pattern analysis and melting peak analysis. Preferably, the melting analysis is a melting curve analysis.

For instance, when the duplex between the SO and the extended strand is melted, the reporter molecule and the quencher molecule on the single-stranded SO are conformationally adjacent to each other to allow the quencher molecule to quench the signal from the reporter molecule, such that change in signals is induced to give the detectable signal. Furthermore, where the SO and the extended strand is re-hybridized to form a duplex, the reporter molecule and the quencher molecule on the SO are conformationally separated to allow the quencher molecule to unquench the signal from the reporter molecule, such that change in signals is induced to give the detectable signal (see FIG. 2).

According to a preferred embodiment, the presence of the extended strand of the PTO fragment is detected by a melting curve analysis using $T_m$ values of the duplex between the SO and the extended strand.

Where $T_m$ values of the duplex between the SO and the extended strand are used for analysis, it is preferable to use labels (e.g., fluorescent labels) allowing for homogeneous assay with no separation of the hybridization resultant between the SO and the extended strand.

According to a preferred embodiment, the hybridization resultant between the SO and the extended strand has $T_m$ values that are adjustable by sequence and/or length of the PTO fragment, sequence and/or length of the CTO, sequence and/or length of the SO and their combination.

For instance, $T_m$ values of the hybridization resultant may be adjusted by adjusting mismatch extent of the sequence of the SO. Furthermore, by adjusting lengths of the SO, $T_m$ values of the hybridization resultant may be also adjusted.

Preferably, the present method further comprises the step of providing a detectable signal between the steps (e) and (f) by melting the hybridization resultant of the step (e) or by melting and hybridizing the hybridization resultant of the step (e); wherein the step (f) is performed by detecting the signal to determine the presence of the extended strand.

Alternatively, the present method further comprises the step of providing and detecting a detectable signal after the step (f) by melting the hybridization resultant of the step (e) or by melting and hybridizing the hybridization resultant of the step (e), whereby the presence of the extended strand is determined one more time.

According to a preferred embodiment, the presence of the extended strand of the PTO fragment is detected by a hybridization curve analysis.

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research,* 6:3543-3547 (1979)) and nearest-neighbor method (SantaLucia J. Jr., et al., *Biochemistry,* 35:3555-3562 (1996)); Sugimoto N., et al., *Nucleic Acids Res.,* 24:4501-4505 (1996)).

According to a preferred embodiment, the $T_m$ value refers to actual $T_m$ values under reaction conditions actually practiced.

The melting curve or hybridization curve may be obtained by conventional technologies, for example, as described in U.S. Pat. Nos. 6,174,670 and 5,789,167, Drobyshev et al, *Gene* 188: 45 (1997); Kochinsky and Mirzabekov *Human Mutation* 19:343 (2002); Livehits et al *J. Biomol. Structure Dynam.* 11:783 (1994); and Howell et al *Nature Biotechnology* 17:87 (1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

A plot of the first derivative of the fluorescence vs. temperature, i.e., a plot of the rate of change in fluorescence vs. temperature (dF/dT vs. T) or (−dF/dT vs. T) provides melting peak.

The formation of the extended strand may be detected by the size of the extended strand. The SO hybridized with the extended strand provides a detectable signal for the detection of the extended strand by the size of the extended strand. For example, where the formation of the extended strand is detected by various electrophoresis methods such as gel electrophoresis and polyacrylamide gel electrophoresis, the SO hybridized with the extended strand provides a signal on a gel matrix indicating the presence of the extended strand. Preferably, the SO with a single fluorescent label is used.

The PTO, CTO and SO may be comprised of naturally occurring dNMPs. Alternatively, the PTO, CTO and SO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO, CTO and SO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the CTO. The strategies using universal bases and degenerate sequences in the CTO ensure to use one type or minimal types of the CTO for screening multiple target nucleic acid sequences.

According to a preferred embodiment, the present method further comprises the step of denaturation between the steps (d) and (e). The extended duplex formed in the step (d) is denatured to a single strand form and then hybridized with the SO.

According to a preferred embodiment, the method further comprises repeating all or some of the steps (a)-(f) with denaturation between repeating cycles. For instance, the method further comprises repeating the steps (a)-(b), (a)-(d) or (a)-(f) with denaturation between repeating cycles. This repetition permits to amplify the target nucleic acid sequence and/or the target signal.

According to a preferred embodiment, the present invention further comprises repeating the steps (a)-(e) with denaturation between repeating cycles, and melting the hybridization resultant of the step (e) or melting and hybridizing the hybridization resultant of the step (e) to provide a detectable signal; wherein the step (f) is performed by detecting the signal to determine the presence of the extended strand.

The denaturation may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

According to a preferred embodiment, the present invention may be carried out by a series of melting analyses to qualitatively or quantitatively detect the target nucleic acid sequence.

More preferably, the present invention comprises (i) repeating the steps (a)-(d) with denaturation between repeating cycles to form the extended strand, (ii) performing a melting analysis of hybridization resultant of the SO and the extended strand and (iii) repeating the steps (i) and (ii) at least twice. In such approach, the melting analysis is repeatedly carried out at least twice in a certain interval.

According to a preferred embodiment, the number of repetition of the steps (a)-(d) may be optionally controlled. In performing a series of melting analyses, the number of repetition of the steps (a)-(d) for a run of a melting analysis may be the same as or different from that of repetition of the steps (a)-(d) for another run of a melting analysis.

It would be understood by one of skill in the art that the repetition of the steps (a)-(d) is an illustrative example for the formation of the extended strand. For instance, the present invention may be carried out by repeating the steps (a)-(b) and performing the steps (c) and (d) to form the extended strand followed by performing a melting analysis.

According to a preferred embodiment, the steps (a)-(f) are performed in a reaction vessel or in separate reaction vessels. For example, the steps (a)-(b), (c)-(d) or (e)-(f) may be performed in separate reaction vessels.

According to a preferred embodiment, the steps (a)-(b) and (c)-(f) may be simultaneously or separately even in a reaction vessel depending on reaction conditions (particularly, temperature).

According to a preferred embodiment, the steps (a)-(b) are repeated with denaturation.

Where the upstream primer is used as the upstream oligonucleotide in the repetition process, the present method is preferably performed in the presence of a downstream primer, preferably, by PCR.

According to a preferred embodiment, at least two melting analyses in the present invention permit to quantitatively detect the target nucleic acid sequence.

The area and height of a melting peak obtained by a melting analysis are dependent on the amount of the extended duplex, providing information on the initial amount of the target nucleic acid sequence.

According to a preferred embodiment, the present invention comprises (i) increasing the number of the extended strand by repetition of the steps (a)-(d) with denaturation between repeating cycles, (ii) performing a melting analysis for the hybridization resultant between the SO and the extended strand and (iii) repeating the steps (i) and (ii) at least twice. The amount of the target nucleic acid sequence may be measured by determining a cycle number of the melting analyses at which a predetermined threshold value over the areas and/or the heights of melting peaks obtained is reached.

Alternatively, the quantification of the target nucleic acid sequence may be accomplished by plotting melting analysis information (e.g. area or height of peaks) against the cycle number of the repetition for increase in the amount of the extended strand.

The present invention does not require that target nucleic acid sequences to be detected and/or amplified have any particular sequence or length, including any DNA (gDNA and cDNA) and RNA molecules.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp: 120-122 (1992), U.S. Pat. No. 5,665,539, Niemeyer et al., Trends in Biotechnology 23 pp: 208-216 (2005), U.S. Pat. Pub. No. 2005/0239108 and Ye et al., Journal of Environmental Science 22 pp: 796-800 (2010)).

The present invention is also useful in detection of a nucleotide variation. Preferably, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a DNA molecule. In other words, the term nucleotide variation includes a wild type and its any mutant type at a particular location in a DNA molecule.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to a preferred embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the CTO, extended and hybridized with the SO to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the CTO, extended and hybridized with the SO to provide the target signal. While, under the controlled conditions, the PTO is not hybridized with a mismatching template having non-complementary sequence in the nucleotide variation position and not cleaved. Preferably, in this case, the complementary sequence to the nucleotide variation in the PTO is positioned at its middle of the 3'-targeting portion of the PTO.

Figure 9:
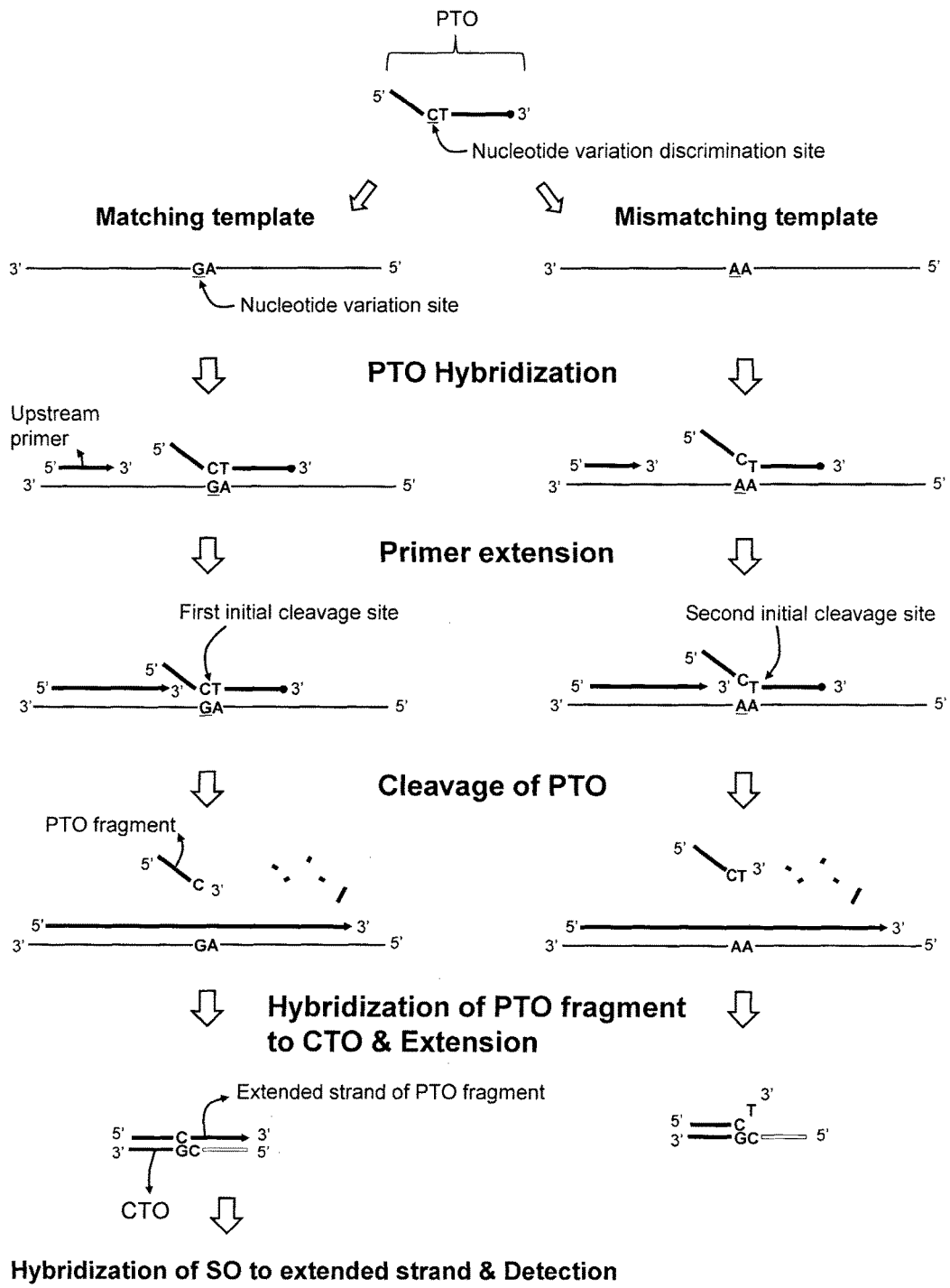
FIG. 9 represents schematically PCE-SH assay for detection of a nucleotide variation.

Alternatively, it is preferable that the 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence (see FIG. 9).

Where a probe having at its 5'-end portion a nucleotide variation discrimination portion is hybridized with a mismatch temple, its 5'-end portion may form a single strand under a certain condition. The probe may correspond to a PTO. The signal may be generated by the present method. This approach may be useful in detection of a target nucleic acid sequence having a nucleotide variation non-complementary to the nucleotide variation discrimination site of probes.

According to a preferred embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to a preferred embodiment, the method is performed in the presence of a downstream primer.

The advantages of the present invention may be highlighted in the simultaneous (multiplex) detection of at least two target nucleic acid sequences.

According to a preferred embodiment, the method is performed to detect at least two types (more preferably, at least three types, still more preferably at least five types) of target nucleic acid sequences.

According to a preferred embodiment, the method is performed to detect at least two types (more preferably, at least three types, still more preferably at least five types) of target nucleic acid sequences; wherein the upstream oligonucleotide comprises at least two types (more preferably at least three types, still more preferably at least five types) of oligonucleotides, the PTO comprises at least two types (more preferably at least three types, still more preferably at least five types) of the PTOs, the CTO comprises at least two types (preferably at least three types, more preferably at least five types) of the CTO, and the SO comprises at least two types (preferably at least three types, more preferably at least five types) of the SO; wherein when at least two types of the target nucleic acid sequences are present, the method provides at least two types of the target signals (the detectable signals) corresponding to the at least two types of the target nucleic acid sequences.

The 5'-tagging portions of the at least two PTOs may have an identical sequence to each other. For instance, where the present invention is carried out for screening target nucleic acid sequences, the 5'-tagging portions of PTOs may have the identical sequence.

Furthermore, a single type of the CTO may used for detection of a plurality of target nucleic acid sequences. For example, where the PTOs having an identical sequence in their 5'-tagging portions are employed for screening target nucleic acid sequences, a single type of the CTO may used.

Where the present invention is performed to simultaneously detect at least two types of the target nucleic acid sequences by melting curve analysis and the hybridization resultant in the step (e) corresponding to the at least two types of the target nucleic acid sequences have different $T_m$ values from each other, it is possible to detect at least two types of the target nucleic acid sequences even using a single type of a label (e.g. FAM).

According to a preferred embodiment, $T_m$ value of the hybrid of SO/extended strand may be adjusted by the sequence and/or length of the SO, the sequence and/or length of a portion of the extended strand to be hybridized with the SO, or combination thereof. Particularly, where the extended strands formed in the present multiplex detection are hybridized with a single type of the SO, $T_m$ values of the hybrids between the extended strands and the SOs are different from each other if the portions of the extended strands to be hybridized with the SOs are designed to have different sequences from each other. Therefore, the multiplex detection may become practical even using a single-typed SO.

The present invention may be performed on a solid phase such as microarray.

According to a preferred embodiment, the present invention is performed on the solid phase and the CTO or the SO is immobilized through its 5'-end or 3'-end onto a solid substrate.

For the solid phase reaction, the CTO or the SO is immobilized directly or indirectly (preferably indirectly) through its 5'-end or 3'-end (preferably the 3'-end) onto the surface of the solid substrate. Furthermore, the CTO or the SO may be immobilized on the surface of the solid substrate in a covalent or non-covalent manner. Where the immobilized CTOs or SOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for CTO or SO immobilization. In addition, poly (T) tail or poly (A) tail may serve as linkers.

According to a preferred embodiment, the solid substrate used in the present invention is a microarray. The microarray to provide a reaction environment in this invention may include any those known to one of skill in the art. All processes of the present invention, hybridization to target nucleic acid sequences, cleavage, extension, melting and fluorescence detection, are carried out on the microarray. The immobilized CTOs or SOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. A plurality of immobilized CTOs or SOs in this invention may be immobilized on an addressable region or two or more addressable regions on a solid substrate that may comprise 2-1,000,000 addressable regions. Immobilized CTOs or SOs may be fabricated to produce array or arrays for a given application by conventional fabrication technologies such as photolithography, ink-jetting, mechanical microspotting, and derivatives thereof.

According to a preferred embodiment, a SO immobilized onto the surface of the solid substrate has an interactive dual label.

In the present invention, a PTO fragment is produced by cleavage of the PTO hybridized with the target nucleic acid and it is annealed to and extended on the CTO, resulting in the formation of an extended strand.

It is also possible to provide additional fragments extendible on the CTO for enhancing the number of the extended strands by an additional 5' nuclease cleavage reaction using an additional PTO which comprises (i) a 3'-targeting portion comprising a hybridizing nucleotide sequence complementary to the extended strand and (ii) a 5'-tagging portion comprising a nucleotide sequence non-complementary to the extended strand but complementary to the capturing portion of the CTO.

Preferably, the additional PTO is located downstream of the SO hybridizing to the extended strand. The SO induces cleavage of the additional PTO by an enzyme having a 5' nuclease activity. When 3'-end of SO is extensible, SO's extended strand induces cleavage of the additional PTO.

The above preferable embodiment has the feature that the formation of the additional fragments is dependent on the formation of an extended strand.

Alternatively, the additional fragments may be provided by using an additional PTO which comprises (i) a 3'-targeting portion comprising a hybridizing nucleotide sequence complementary to the templating portion of CTO and (ii) a 5'-tagging portion comprising a nucleotide sequence non-complementary to the templating portion of CTO but complementary to the capturing portion of the CTO.

Preferable Embodiment with Amplification of a Target Nucleic Acid Sequence

Preferably, the present invention is carried out simultaneously with amplification of a target nucleic acid sequence using a primer pair composed of an upstream primer and a downstream primer capable of synthesizing the target nucleic acid sequence.

In another aspect of this invention, there is provided a method for detecting a target nucleic acid sequence from a DNA or a mixture of nucleic acids by a PCE-SH (PTO Cleavage and Extension-Dependent Signaling Oligonucleotide Hybridization) assay, comprising:

(a) hybridizing the target nucleic acid sequence with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequences; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to a template-dependent nucleic acid polymerase having a 5' nuclease activity under conditions for extension of the primers and for cleavage of the PTO; wherein when the PTO is hybridized with the target nucleic acid sequence, the upstream primer is extended and the extended strand induces cleavage of the PTO by the template-dependent nucleic acid polymerase having the 5' nuclease activity such that the cleavage releases a fragment comprising the 5'-tagging portion or a part of the 5'-tagging portion of the PTO;

(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;

(e) hybridizing the extended strand with a signaling oligonucleotide (SO); wherein the SO comprises a complementary sequence to the extended strand and at least one label; the SO provides a detectable signal by hybridization with the extended strand; and (f) detecting the signal; whereby the detection of the signal indicates the presence of the extended strand and the presence of the target nucleic acid sequence.

Since the preferable embodiment of the present invention follows the steps of the present method described above, the common descriptions between them are omitted in order to avoid undue redundancy leading to the complexity of this specification.

According to a preferred embodiment, the method further comprises repeating all or some of the steps (a)-(f) with denaturation between repeating cycles. For instance, the method further comprises repeating the steps (a)-(b), (a)-(d) or (a)-(f) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to a preferred embodiment, the method is performed to detect at least two types of target nucleic acid sequences.

Target Detection Process by PCE-SH Assay Based on Upstream Oligonucleotide-Independent 5' Nuclease Activity The present invention may be carried out with no use of upstream oligonucleotides.

In a still another aspect of the present invention, there is provided a method for detecting a target nucleic acid sequence from a DNA or a mixture of nucleic acids by a PCE-SH (PTO Cleavage and Extension-Dependent Signaling Oligonucleotide Hybridization) assay, comprising:

(a) hybridizing the target nucleic acid sequence with a probing and targeting oligonucleotide (PTO); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO is cleaved by the enzyme having the 5' nuclease activity such that the cleavage releases a fragment comprising the 5'-tagging portion or a part of the 5'-tagging portion of the PTO;

(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;

(e) hybridizing the extended strand with a signaling oligonucleotide (SO); wherein the SO comprises a complementary sequence to the extended strand and at least one label; the SO provides a detectable signal by hybridization with the extended strand; and (f) detecting the signal; whereby the detection of the signal indicates the presence of the extended strand and the presence of the target nucleic acid sequence.

Considering amplification of target nucleic acid sequences and cleavage efficiency of the PTO, the PCE-SH assay of the present invention is preferably performed using upstream oligonucleotides.

Nucleotide Variation Detection Process by a PCE-SH Assay

In a further aspect of the present invention, there is provided a method for detecting a nucleotide variation on a target nucleic acid sequence by a PCE-SH (PTO Cleavage and Extension-Dependent Signaling Oligonucleotide Hybridization) assay, comprising:

(a) hybridizing the target nucleic acid sequence with an upstream oligonucleotide and a probing and targeting oligonucleotide (PTO); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence, (ii) a 5'-tagging portion comprising a nucleotide sequence non-complementary to the target nucleic acid sequence, and (iii) a nucleotide variation discrimination site, comprising a complementary sequence to the nucleotide variation on the target nucleic acid, positioned on a 5'-end part of the 3'-targeting portion; wherein the 3'-targeting portion is hybridized with the target nucleic acid sequence and the 5'-tagging portion is not hybridized with the target nucleic acid sequence; the upstream oligonucleotide is located upstream of the PTO; the upstream oligonucleotide or its extended strand induces cleavage of the PTO by an enzyme having a 5' nuclease activity;

(b) contacting the resultant of the step (a) to an enzyme having a 5' nuclease activity under conditions for cleavage of the PTO; wherein when the PTO is hybridized with the target nucleic acid sequence having the nucleotide variation complementary to the nucleotide variation discrimination site, and the 5'-end part of the 3'-targeting portion forms a double strand with the target nucleic acid sequence to induce cleavage from a first initial cleavage site, a first fragment is released; wherein when the PTO is hybridized with a target nucleic acid sequence having a nucleotide variation non-complementary to the nucleotide variation discrimination site, and the 5'-end part of the 3'-targeting portion does not form a double strand with the target nucleic acid sequence to induce cleavage from a second initial cleavage site located downstream of the first initial cleavage site, a second fragment is released; wherein the second fragment comprises an additional 3'-end portion allowing the second fragment different from the first fragment;

(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the first fragment or the second fragment released from the PTO is hybridized with the capturing portion of the CTO;

(d) performing an extension reaction using the resultant of the step (c) and a template-dependent nucleic acid polymerase; wherein when the first fragment is hybridized with the capturing portion of the CTO, it is extended to form an extended strand comprising a extended sequence complementary to the templating portion of the CTO; wherein when the second fragment is hybridized with the capturing portion of the CTO, it is not extended;

(e) hybridizing the extended strand with a signaling oligonucleotide (SO); wherein the SO comprises a complementary sequence to the extended strand and at least one label; the SO provides a detectable signal by hybridization with the extended strand; and (f) detecting the signal; whereby the detection of the signal indicates the presence of the nucleotide variation complementary to the nucleotide discrimination site of the PTO.

The present inventors have found that the probe cleavage site is adjustable depending on the presence and absence of nucleotide variations of interest and the fragments released by cleavage in different sites are distinguished by the ability of extension on an artificial template.

The present invention employs successive events followed by probe hybridization; cleavage of the PTO and extension; formation of a nucleotide variation-dependent extended strand; and detection of the extended strand using a signaling oligonucleotide. Therefore, it is named as VD-PCE-SH (Variation Detection by PTO Cleavage and Extension-Dependent Signaling Oligonucleotide Hybridization) assay.

According to a preferred embodiment, the nucleotide variation detected by the present invention is a variation by a single nucleotide such as SNR In the present application, a target nucleic acid sequence having a nucleotide variation complementary to the nucleotide variation discrimination site of the PTO is also described as "match template". A target nucleic acid sequence having a nucleotide variation non-complementary to the nucleotide variation discrimination site of the PTO is also described as "mismatch template".

According to a preferred embodiment, the term "non-complementary" in conjunction with a nucleotide variation non-complementary to the nucleotide variation discrimination site is used herein to encompass non-complementarity due to insertion or deletion.

The VD-PCE-SH assay of the present invention uses the PTO having the nucleotide variation discrimination site positioned on the 5'-end part of the 3'-targeting portion for selectivity of the PTO to a specific nucleotide variation. Where the PTO is hybridized with the target nucleic acid sequence (i.e., match template) having the nucleotide variation complementary to the nucleotide variation discrimination site, the 5'-end part of the 3'-targeting portion forms a double strand with the match template; however, where the PTO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

It is noteworthy that such distinct hybridization patterns on the nucleotide variation of interest are responsible for differences in initial cleavage sites of the PTO, thereby producing two types of PTO fragments to give signal differentiation depending on the presence of the nucleotide variation of interest.

A first fragment is generated by cleavage of hybrid between the PTO and matching template and a second fragment is generate by cleavage of hybrid between the PTO and mismatching template, respectively. The second fragment comprises an additional 3'-end portion rendering the second fragment to be different from the first fragment.

The production of either the first fragment or the second fragment may be distinctly detected by an extension reaction on the CTO.

Generally, the hybridization between a 3'-end part of primers and a template is very crucial to extension of primers in a stringent condition. In the present invention, the first fragment and the second fragment each is hybridized with the same site of the CTO. As described above, the second fragment comprises the additional 3'-end portion compared with the first fragment. By adjusting hybridization conditions and a sequence of the CTO opposed to the additional 3'-end portion of the second fragment, only the first fragment may be permitted to extend.

According to a preferred embodiment, the CTO has a sequence selected such that the CTO is not hybridized with the additional 3'-end portion of the second fragment to prevent the second fragment from extension when the second fragment is hybridized with the capturing portion of the CTO.

According to a preferred embodiment, the sequence of the CTO opposed to the additional 3'-end portion of the second fragment is non-complementary to the additional 3'-end portion.

The production of the extended strand by extension of the first fragment may be detected by using SO as the present invention described above.

According to conventional technologies using 5' nuclease activities for detection of nucleotide variations, hybridization of probes used is determined or affected by a whole sequence of a probe. In such conventional technologies, probe design and construction, and optimization of reaction conditions are very troublesome as hybridization of probes dependent on the presence of nucleotide variations is compelled to be mainly determined by difference by one nucleotide.

According to the VD-PCE-SH assay, a nucleotide variation discrimination site is positioned on a 5'-end part of a hybridization-involving portion of probes, enabling optimization of hybridization conditions to be convenient. In addition, the VD-PCE-SH assay differentially detects a nucleotide variation by a local portion of probes rather than a whole sequence of probes, such that the difference by even one nucleotide such as SNPs may be accurately detected.

It has been known to one of skill in the art that a probe sequence adjacent to a sequence opposed to a SNP extremely affects probe hybridization. The conventional probes have a sequence opposed to a SNP generally in their middle portion. In this regard, the conventional probes may not select a surrounding sequence around a SNP involved in hybridization. The conventional technologies have serious limitations due to surrounding sequences to SNPs.

The VD-PCE-SH assay of the present invention will be described in more detail as follows:

Since the VD-PCE-SH assay of the present invention is one of applications of the PCE-SH assay described above, the common descriptions between them are omitted in order to avoid undue redundancy leading to the complexity of this specification.

Step (a): Hybridization of an Upstream Oligonucleotide and a PTO with a Target Nucleic Acid Sequence According to the present invention, a target nucleic acid sequence is first hybridized with an upstream oligonucleotide and a PTO.

The PTO used in the detection of nucleotide variations comprises (i) a 3'-targeting portion serving as a probe, (ii) a 5'-tagging portion with a nucleotide sequence non-complementary to the target nucleic acid sequence, and (iii) a nucleotide variation discrimination site, comprising a complementary sequence to the nucleotide variation on the target nucleic acid, positioned on a 5'-end part of the 3'-targeting portion. The 5'-tagging portion is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 9.

The PTO comprises the nucleotide variation discrimination site comprising a complementary sequence to the nucleotide variation positioned on a 5'-end part of the 3'-targeting portion.

Where the PTO is hybridized with the target nucleic acid sequence having the nucleotide variation complementary to the variation discrimination site, the 5'-end part of the 3'-targeting portion forms a double strand with the target nucleic acid sequence. Where the PTO is hybridized with a target nucleic acid sequence having a nucleotide variation non-complementary to the variation discrimination site, the 5'-end part of the 3'-targeting portion does not form a double strand with the target nucleic acid sequence. Such distinct hybridization patterns on the nucleotide variation of interest are responsible for differences in cleavage sites of the PTO, thereby producing two types of PTO fragments to give signal differentiation depending on the presence of the nucleotide variation of interest. The 5'-end part of the 3'-targeting portion of the PTO may be also described as a single strand-forming 5'-end portion of the 3'-targeting portion of the PTO when hybridized with a target nucleic acid sequence having a nucleotide variation non-complementary to the variation discrimination site.

The nucleotide variation discrimination site positioned on a 5'-end part of the 3'-targeting portion of the PTO comprises a complementary sequence to the nucleotide variation. For instance, where a nucleotide variation to be detected is a SNP, the nucleotide variation discrimination site comprises a complementary nucleotide to the SNP.

According to a preferred embodiment, the nucleotide variation discrimination site is located within 10 nucleotides, more preferably 8 nucleotides, still more preferably 6 nucleotides, still much more preferably 4 nucleotides, 3 nucleotides, 2 nucleotides or 1 nucleotide apart from the 5'-end of the 3'-targeting portion of the PTO. Preferably, the nucleotide variation discrimination site is located at the 5'-end of the 3'-targeting portion of the PTO.

The term "site" with reference to either nucleotide variation discrimination site of probes or nucleotide variation site on target sequences is used herein to encompass not only a single nucleotide but also a plurality of nucleotides.

Preferably, the hybridization in step (a) is preformed under stringent conditions that the 3'-targeting portion is hybridized with the target nucleic acid sequence and the 5'-tagging portion is not hybridized with the target nucleic acid sequence.

Step (b): Release of a Fragment from the PTO

Afterwards, the resultant of the step (a) is contacted to an enzyme having a 5' nuclease activity under conditions for cleavage of the PTO.

Where the PTO is hybridized with the target nucleic acid sequence (i.e., match template) having the nucleotide variation complementary to the variation discrimination site, and the 5'-end part of the 3'-targeting portion forms a double strand with the target nucleic acid sequence to induce cleavage from a first initial cleavage site, a first fragment is released (see FIG. 9).

Where the PTO is hybridized with a target nucleic acid sequence (i.e., mismatch template) having a nucleotide variation non-complementary to the variation discrimination site, and the 5'-end part of the 3'-targeting portion does not form a double strand with the target nucleic acid sequence to induce cleavage from a second initial cleavage site located downstream of the first initial cleavage site, a second fragment is released; wherein the second fragment comprises an additional 3'-end portion allowing the second fragment different from the first fragment (see FIG. 9).

Where the target nucleic acid sequence is not present in a sample, the cleavage of the PTO does not occur.

As such, differences in cleavage sites and types of PTO fragments generated result in different extension patterns depending on the presence and absence of the nucleotide variation of interest on the target nucleic acid sequence, contributing to differential detection of the nucleotide variation on the target nucleic acid sequence.

A cleavage site by extension of upstream primers is generally positioned in a 5' to 3' direction at an initial nucleotide of a double strand (i.e., bifurcation site) in structures including a single strand and a double strand or at 1-2 nucleotides apart from the initial nucleotide. By the cleavage reaction, fragments comprising the 5'-tagging portion and a part of the 3'-targeting portion are produced. Where the present invention is performed by upstream oligonucleotide extension-independent cleavage induction, the cleavage site of the PTO may be adjusted by location of upstream oligonucleotides.

The term used herein "a first initial cleavage site" in conjunction with the PTO means to a cleavage site of the PTO being firstly cleaved when the PTO is hybridized with the target nucleic acid sequence having the nucleotide variation complementary to the variation discrimination site. The term used herein "a second initial cleavage site" in conjunction with the PTO means to a cleavage site of the PTO being firstly cleaved when the PTO is hybridized with a target nucleic acid sequence having a nucleotide variation non-complementary to the variation discrimination site.

The term used herein "a first fragment" refers to a fragment produced upon cleavage at the first initial cleavage site. The term is used interchangeably with "a first segment" and "a PTO first fragment". The term herein "a second fragment" refers to a fragment produced upon cleavage at the second initial cleavage site. The term is used interchangeably with "a second segment" and "a PTO second fragment".

Preferably, the first fragment and the second fragment each comprises the 5'-tagging portion or a part of the 5'-tagging portion.

The cleavage may successively occur after the cleavage of the first initial cleavage site (or the second initial cleavage site) depending on cleavage methods used. For instance, where a 5' nuclease cleavage reaction together with extension of upstream primers is used, the initial cleavage site and its successive sequence are cleaved. Where an upstream probe is used and the cleavage reaction occurs at a site apart from a location site of the probe, the cleavage reaction may occur only at the site and cleavage at successive sites may not occur.

According to a preferred embodiment, an initial cleavage site dependent on extension of upstream primers may be positioned in a 5' to 3' direction at an initial nucleotide of a double strand (i.e., bifurcation site).

As shown in FIG. 9 representing an example of the present invention, the nucleotide variation discrimination site is positioned at the 5'-end of the 5'-end part of the 3'-targeting portion. In such case, the first initial cleavage site is positioned immediately adjacent, in a 5' to 3' direction, to the 5'-end part of the 3'-targeting portion. In other words, the first initial cleavage site is positioned immediately adjacent, in a 3' direction, to the nucleotide variation discrimination site. The second initial cleavage site is generally positioned at 1 nucleotide apart, in a 3' direction, from the nucleotide variation discrimination site.

Where the nucleotide variation discrimination site is positioned at 1 nucleotide apart from the 5'-end of the 5'-end part of the 3'-targeting portion, the first initial cleavage site is positioned immediately adjacent, in a 5' direction, to the nucleotide variation discrimination site. The second initial cleavage site is generally positioned at 1 nucleotide apart, in a 3' direction, from the nucleotide variation discrimination site.

According to a preferred embodiment, the 5'-end part may partially comprise a non-hybridizable sequence (or a non-base pairing sequence). The introduction of a non-hybridizable sequence into the 5'-end part is very advantageous over single strand formation of the 5'-end part when the PTO is hybridized with a target nucleic acid sequence having a nucleotide variation non-complementary to the nucleotide variation discrimination site. In addition, the introduction of a non-hybridizable sequence enables the second initial cleavage site to be adjusted.

According to a preferred embodiment, the 5'-end part of the 3'-targeting portion of the PTO comprises a non-base pairing moiety located within 1-10 nucleotides (more preferably 1-5 nucleotides) apart from the nucleotide variation discrimination site. The non-base pairing moiety prevents the 5'-end part of the 3'-targeting portion from formation of a double strand with the target nucleotide sequence when the PTO is hybridized with the target nucleic acid sequence having the nucleotide variation non-complementary to the variation discrimination site.

The use of the non-base pairing moiety (e.g., mismatch nucleotide) enhances discrimination potential of the PTO to nucleotide variations.

According to a preferred embodiment, the non-base pairing moiety does not inhibit the formation of a double strand between the 5'-end part and the target nucleic acid sequence when the PTO is hybridized with the target nucleic acid sequence having the nucleotide variation complementary to the nucleotide variation discrimination site.

According to a preferred embodiment, the non-base pairing moiety widens the distance between the first initial cleavage site and the second initial cleavage site.

Preferably, the non-base pairing moiety is located downstream of the nucleotide variation discrimination site.

For example, where a mismatch nucleotide as a non-base pairing moiety is introduced into a position 2 nucleotides apart, in a 3' direction, from the nucleotide variation discrimination site, the second initial cleavage site is adjusted to a position 2 nucleotides apart from the nucleotide variation discrimination site. In case of not using the mismatch nucleotide, the second initial cleavage site is positioned 1 nucleotide apart from the nucleotide variation discrimination site. That is to say, the non-base pairing moiety may widen the distance between the first initial cleavage site and the second initial cleavage site.

The non-base pairing moiety includes any moieties not forming a base pair between target nucleic acid sequences. Preferably, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part has preferably 1-10, more preferably 1-5, still more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to a preferred embodiment, the nucleotide variation discrimination site and the non-base pairing moiety of the PTO are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

Alternatively, the cleavage reaction may be executed only at the first initial cleavage site not at the second initial cleavage site. For instance, where an upstream probe is used and the cleavage reaction occurs at a site apart from a location site of the probe, the cleavage reaction may occur only at the first initial cleavage site when the PTO is hybridized with the match template. When the PTO is hybridized with the mismatch template, the bifurcation site (the second initial cleavage site) may not be cleaved because of a long distance from the upstream probe.

According to a preferred embodiment, where the PTO is hybridized with the mismatch template, the second initial cleavage site comprises an initial site of a double strand (i.e., bifurcation site) in structures including a single strand and a double strand.

According to an embodiment, the PTO has a blocker portion containing as a blocker at least one nucleotide resistant to cleavage by the enzyme having 5' nuclease activity and the blocker portion is positioned at the second initial cleavage site. The blocker portion prevents cleavage at the second initial cleavage site and successive cleavages.

The number of blockers contained in the blocker portion may be not limited, preferably, 1-10, more preferably 2-10, still more preferably 3-8, most preferably 3-6 blockers. The blockers present in the probes may be in a continuous or intermittent manner, preferably a continuous manner. The nucleotides as blockers with a backbone resistant to the 5' to 3' exonuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

Step (c): Hybridization of the Fragment Released from the PTO with CTO

The fragment released from the PTO is hybridized with a CTO (Capturing and Templating Oligonucleotide).

The first fragment and the second fragment have commonly a hybridizable sequence with the capturing portion of the CTO and thus one of them is hybridized with the CTO.

The second fragment produced when hybridized with the mismatch template comprises an additional 3'-end portion being different from the first fragment produced when hybridized with the match template.

According to a preferred embodiment, the CTO has a sequence selected such that the CTO is not hybridized with the additional 3'-end portion of the second fragment to prevent the second fragment from extension when the second fragment is hybridized with the capturing portion of the CTO. For example, the sequence of the CTO may be selected such that the CTO has a mismatch nucleotide(s) opposed to the additional 3'-end portion of the second fragment. Alternatively, universal bases may be used instead of the mismatch nucleotide.

The first initial cleavage site (or the second initial cleavage site) may not be fixed but rather multiple in a condition. For example, initial cleavage sites may be positioned in a 5' to 3' direction at an initial nucleotide of a double strand (i.e., bifurcation site) in structures including a single strand and a double strand and 1-2 nucleotides apart from the initial nucleotide. In such case, preferably, the sequence of the CTO is selected such that the shortest fragment released by the first initial cleavage is selectively extended in the present invention to generate the extended strand indicative of the presence of the nucleotide variation.

Step (d): Extension of the Fragment

When the first fragment is hybridized with the capturing portion of the CTO, it is extended to form an extended strand comprising an extended sequence complementary to the templating portion of the CTO. When the second fragment is hybridized with the capturing portion of the CTO, it is not extended.

Generally, the extension of primers may be controlled by hybridization between a 3'-end part of primers and a template. By adjusting primer sequences and reaction conditions (e.g. annealing temperature), the extension of primers having at their 3'-end part 1-3 mismatch nucleotides is allowable. Alternatively, the extension of primers may be allowable only when they have perfectly complementary sequence to target sequences.

According to a preferred embodiment, the sequence of the CTO is selected that either the first fragment or the second fragment is selectively extended.

According to a preferred embodiment, the extension of the fragment is carried out under conditions such that the extension does not occur even when a single mismatch is present at the 3'-end part of the fragment.

Step (e): Signal Generation by Hybridization Between the Extended Strand and SO

Following the extension reaction, the extended strand is hybridized with a signaling oligonucleotide (SO). The signal indicative of the presence of the nucleotide variation complementary to the nucleotide discrimination site of the PTO is provided.

Details of hybridization between the extended strand and the SO, labeling systems and signal generation will be described with reference to descriptions indicated above.

Step (f): Detection of Signal

Finally, the detectable signal provided in the step (e) is detected, whereby the detection of the signal indicates the presence of the extended strand and the presence of the nucleotide variation complementary to the nucleotide discrimination site of the PTO.

Details of the detection of the signal will be described with reference to descriptions indicated above.

According to an embodiment, the present invention for nucleotide variation detection may be performed with no help of upstream oligonucleotides. Enzymes having upstream oligonucleotide-independent 5' nuclease activity are used. Considering amplification of target nucleic acid sequences, reaction conditions and 5' nuclease activity, the present invention is preferably performed using upstream oligonucleotides, more preferably upstream primers.

Kits for Target Detection

In a further aspect of this invention, there is provided a kit for detecting a target nucleic acid sequence from a DNA or a mixture of nucleic acids by a PCE-SH (PTO Cleavage and Extension-Dependent Signaling Oligonucleotide Hybridization) assay, comprising:

(a) a probing and targeting oligonucleotide (PTO); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence;

(b) an upstream oligonucleotide comprising a hybridizing nucleotide sequence complementary to the target nucleic acid sequence; wherein the upstream oligonucleotide is located upstream of the PTO; wherein the upstream oligonucleotide or its extended strand induces cleavage of the PTO by an enzyme having a 5' nuclease activity such that the cleavage releases a fragment comprising the 5'-tagging portion or a part of the 5'-tagging portion of the PTO;

(c) a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; wherein the fragment hybridized with the capturing portion of the CTO is extended to form an extended strand comprising an extended sequence complementary to the templating portion of the CTO, thereby forming an extended duplex; and (d) a signaling oligonucleotide (SO); wherein the SO comprises a complementary sequence to the extended strand and at least one label; the SO provides a detectable signal by hybridization with the extended strand.

Since the kit of this invention is constructed to perform the detection method of the present invention described above, the common descriptions between them are omitted in order to avoid undue redundancy leading to the complexity of this specification.

According to a preferred embodiment, at least a portion of the SO comprises a complementary sequence to the extended sequence.

According to a preferred embodiment, the kit comprises (i) the label linked to the SO, (ii) a combination of the label linked to the SO and a label linked to the fragment from the PTO, (iii) a combination of the label linked to the SO and a label to be incorporated into the extended strand, or (iv) a combination of the label linked to the SO and an intercalating dye.

According to a preferred embodiment, the SO is labeled with an interactive dual label comprising a reporter molecule and a quencher molecule.

According to a preferred embodiment, the SO is labeled with a single label.

According to a preferred embodiment, the kit further comprises an additional SO comprising a complementary sequence to the extended strand, the two SOs are hybridized with the extended strand in an adjacent manner, the two SOs each comprises one label among a reporter molecule and a quencher molecule of an interactive dual label.

According to a preferred embodiment, the SO comprises one label among a reporter molecule and a quencher molecule of an interactive dual label and the fragment from the PTO comprises the other label among the reporter molecule and the quencher molecule.

According to a preferred embodiment, the SO comprises one label among a reporter molecule and a quencher molecule of an interactive dual label, and the templating portion of the CTO comprises a nucleotide having a first non-natural base; wherein the kit further comprises a nucleotide having both a second non-natural base with a specific binding affinity to the first non-natural base and the other among the reporter molecule and the quencher molecule.

According to a preferred embodiment, the SO comprises one label among a reporter molecule and a quencher molecule of an interactive dual label, and the kit further comprises a nucleotide having the other among the reporter molecule and the quencher molecule.

According to a preferred embodiment, the SO comprises an acceptor of a FRET (fluorescence resonance energy transfer) and the kit further comprises an intercalating dye.

According to a preferred embodiment, the PTO, CTO and/or SO is blocked at its 3'-end to prohibit its extension.

According to a preferred embodiment, the upstream oligonucleotide is an upstream primer or an upstream probe.

According to a preferred embodiment, the kit further comprises an enzyme having a 5' nuclease activity.

According to a preferred embodiment, the kit is for detection of at least two types of target nucleic acid sequences; wherein the upstream oligonucleotide comprises at least two types of oligonucleotides, the PTO comprises at least two types of the PTOs, the CTO comprises at least two types of the CTOs and the SO comprises at least two types of the SOs.

According to a preferred embodiment, the kit further comprises a downstream primer.

The features and advantages of this invention will be summarized as follows:

(a) The present invention does not use probes to be hybridized with target nucleic acid sequences for providing target signals. Interestingly, the present invention uses probes (signaling oligonucleotides) to be hybridized with the extended strand formed in a target-dependent manner in which the extended strand is synthesized using the CTO artificially selected as templates. The present invention employs firstly the PTO for probing target nucleic acid sequences and then secondly the SO for providing signals by hybridization with the target-dependent extended strand, contributing to dramatic increase in specificity and much better convenience in determining reaction conditions by adjusting conditions for signal generation irrespective of target nucleic acid sequences. Such features permit conditions for signal generation to be more readily established in simultaneous multiplex target detection in diverse clinical samples, and false positive signals to be prevented.

(b) In conventional technologies using probes to be hybridized with target nucleic acid sequences, probes are hybridized with target nucleic acid sequences in competition with complementary sequences of target nucleic acid sequences. However, the present invention is able to amplify only the extended strand using a controlled amount of the CTO as templates and therefore ensure efficient hybridization of probes, making it possible to efficiently give signals indicative of the presence of target nucleic acid sequences.

(c) The present invention may detect the presence of target nucleic acid sequences in a real-time manner or by a melting analysis.

(d) The $T_m$ value of the hybridization resultant between the extended strand and the SO may be adjustable by a sequence and/or length of the SO and therefore arbitrarily pre-determined. By using such feature, (i) the present invention may detect target nucleic acid sequences with differentiating false positive signals because signals generated at temperatures other than pre-determined $T_m$ values correspond to false positive signals. (ii) The arbitrary determination of $T_m$ values of the hybridization resultant becomes more advantageous in multiplex detection for at least two target nucleic acid sequences.

(e) $T_m$ value of conventional melting curve analysis of the hybrid between a probe and a target nucleic acid sequence is affected by a sequence variation on the target nucleic acid sequence. However, an extended strand in the present invention provides a constant $T_m$ value regardless of a sequence variation on the target nucleic acid sequences, permitting to ensure excellent accuracy in melting curve analysis.

(f) It is noteworthy that the sequences of the 5'-tagging portion of the PTO, the CTO and the SO can be selected with no consideration of target nucleic acid sequences. This makes it possible to pre-design a pool of sequences for the 5'-tagging portion of the PTO, the CTO and the SO. Although the 3'-targeting portion of the PTO has to be prepared with considering target nucleic acid sequences, the CTO and the SO can be prepared in a ready-made fashion with no consideration or knowledge of target nucleic acid sequences.

(g) A wide variety of the conventional labeled probes are applicable to the present invention for target detection.

(h) Where the hybridization resultants between the extended strands and the SOs have different $T_m$ values from each other, at least two target nucleic acid sequences may be detected by melting curve analysis even using a labeling system providing signals with the same fluorescence characteristics. The advantage permits to be free from limitations associated with the number of detectable fluorescence labels in multiplex real-time detection.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of PTO Cleavage and Extension-Dependent Signaling Oligonucleotide Hybridization (PCE-SH) Assay A New assay, PTO Cleavage and Extension-Dependent Signaling Oligonucleotide Hybridization (PCE-SH) assay, was evaluated for the detection of a target nucleic acid sequence in (i) real-time detection at a pre-determined temperature or (ii) melting analysis manner (see FIG. 2).

Taq DNA polymerase having a 5' nuclease activity was used for the extension of upstream primer, the cleavage of PTO, and the extension of PTO fragment.

PTO and CTO have no label. PTO and CTO are blocked with a carbon spacer at their 3'-ends. The synthetic oligonucleotide for *Neisseria gonorrhoeae* (NG) gene was used as a target template. Signaling oligonucleotide (SO) has a fluorescent reporter molecule (CAL Fluor Red 610) at its 5'-end and has a quencher molecule (BHQ-2) at its 3'-end.

The sequences of synthetic template, upstream primer, PTO, CTO and SO used in this Example are:

```
NGT
                                     (SEQ ID NO: 1)
5'-AAATATGCGAAACACGCCAATGAGGGGCATGATGC
TTTCTTTTTGTTCTTGCTCGGCAGAGCGAGTGATACCG
ATCCATTGAAAAA-3'

NG-R
                                     (SEQ ID NO: 2)
5'-CAATGGATCGGTATCACTCGC-3'

NG-PTO
                                     (SEQ ID NO: 3)
5'-ACGACGGCTTGGCTGCCCCTCATTGGCGTGTTTCG
[C3 spacer]-3'

NG-CTO
                                     (SEQ ID NO: 4)
5'-GCGCTGGATACCCTGGACGATATGCAGCCAAGCCG
TCGT[C3 spacer]-3'

NG-SO-1
                                     (SEQ ID NO: 5)
5'-[CAL Fluor Red 610]GCGCTGGATACCCTGG
ACGATATG[BHQ-2]-3'
(Underlined letters indicate the
5'-tagging portion of PTO)
```

1-1. Real-Time Detection at a Pre-Determined Temperature

The reaction was conducted in the final volume of 20 μl containing 2 pmole of synthetic template (SEQ ID NO: 1) for NG gene, 10 pmole of upstream primer (SEQ ID NO: 2), 5 pmole of PTO (SEQ ID NO: 3), 0.5 pmole of CTO (SEQ ID NO: 4), 0.5 pmole of SO (SEQ ID NO: 5) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., and 30 sec at 72° C. Detection of the generated signal was performed at the hybridization step (60° C.) of each cycle. The detection temperature was determined to the extent that the extended strand-SO hybrid maintains a double-stranded form.

As shown FIG. 10A, the fluorescent signal was detected in the presence of the template. No signal was detected in the absence of the template, PTO, CTO or SO.

1-2. Melting Analysis

After the reaction in Example 1-1, melting curve was obtained by cooling the reaction mixture to 55° C., holding at 55° C. for 30 sec, and heating slowly at 55° C. to 85° C. The fluorescence was measured continuously during the temperature rise to monitor dissociation of an extended strand-SO hybrid. Melting peak was derived from the melting curve data.

As shown FIG. 10B, a peak at 68.5° C. corresponding to the expected Tm value of the extended strand-SO hybrid was detected in the presence of template. No peak was detected in the absence of the template, PTO, CTO or SO.

Example 2: Detection of a Target Nucleic Acid Sequence Using PCE-SH Assay

We further examined whether PCE-SH assay can detect a target nucleic acid sequence in (i) real-time PCR manner or (ii) post-PCR melting analysis manner.

Taq DNA polymerase having a 5' nuclease activity was used for the extension of upstream primer and downstream primer, the cleavage of PTO and the extension of PTO fragment.

PTO and CTO have no label. PTO and CTO are blocked with a carbon spacer at their 3'-ends. The genomic DNA of NG gene was used as a target template. SO has a fluorescent reporter molecule (CAL Fluor Red 610) at its 5'-end and has a quencher molecule (BHQ-2) at its 3'-end.

The sequences of upstream primer, downstream primer, PTO, CTO and SO used in this Example are:

```
NG-F
                                        (SEQ ID NO: 6)
5'-TACGCCTGCTACTTTCACGCT-3'

NG-R
                                        (SEQ ID NO: 2)
5'-CAATGGATCGGTATCACTCGC-3'

NG-PTO
                                        (SEQ ID NO: 3)
5'-ACGACGGCTTGGCTGCCCCTCATTGGCGTGTTTCG
[C3 spacer]-3'

NG-CTO
                                        (SEQ ID NO: 4)
5'-GCGCTGGATACCCTGGACGATATGCAGCCAAGCCG
TCGT[C3 spacer]-3'

NG-SO-1
                                        (SEQ ID NO: 5)
5'-[CAL Fluor Red 610]GCGCTGGATACCCTGG
ACGATATG[BHQ-2]-3'
(Underlined letters indicate the
5'-tagging portion of PTO)
```

2-1. Real-Time Detection at a Pre-Determined Temperature During PCR

The reaction was conducted in the final volume of 20 μl containing 100 pg of genomic DNA of NG, 10 pmole of upstream primer (SEQ ID NO: 2), 10 pmole of downstream primer (SEQ ID NO: 6), 5 pmole of PTO (SEQ ID NO: 3), 0.5 pmole of CTO (SEQ ID NO: 4), 0.5 pmole of SO (SEQ ID NO: 5) and 10 μl of 2× Master Mix containing 2.5 mM MgCl$_2$, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 60° C., and 30 sec at 72° C. Detection of the signal was performed at the hybridization step (60° C.) of each cycle. The detection temperature was determined to the extent that the extended strand-SO hybrid maintains a double-stranded form.

As shown FIG. 11A, the fluorescent signal (Ct: 30.34) was detected in the presence of the template. No signal was detected in the absence of the template.

2-2. Post-PCR Melting Analysis

After the reaction in Example 2-1, melting curve was obtained by cooling the reaction mixture to 55° C., holding at 55° C. for 30 sec, and heating slowly at 55° C. to 85° C. The fluorescence was measured continuously during the temperature rise to monitor dissociation of an extended strand-SO hybrid. Melting peak was derived from the melting curve data.

As shown FIG. 11B, a peak at 68.5° C. corresponding to the expected Tm value of the extended strand-SO hybrid was detected in the presence of template. No peak was detected in the absence of the template.

Example 3: Discrimination of a Single Nucleotide Variation of a Target Nucleic Acid Sequence Using PCE-SH We further examined whether PCE-SH assay can discriminate a single nucleotide variation of a target nucleic acid sequence.

Taq DNA polymerase having a 5' nuclease activity was used for the extension of upstream primer and downstream primer, the cleavage of PTO and the extension of PTO fragment. PTO and CTO have no label. PTO and CTO are blocked with a carbon spacer at their 3'-ends. Wild-type (C), hetero-type (C/T) and mutant-type (T) of human genomic DNA for C677T mutation of MTHFR gene were used as target nucleic acids. SO has a quencher molecule (BHQ-2) at its 5'-end and has a fluorescent reporter molecule (CAL Fluor Red 610) at its 3'-end.

PTO-1(SEQ ID NO:9) and CTO-1 (SEQ ID NO:11) were used to detect the wild-type, and PTO-2(SEQ ID NO:10) and CTO-2(SEQ ID NO:12) used to detect the mutant-type. Where the wild-type gene was present, the extended strand (hereinafter referred to as "wild-type extended strand") was formed using CTO-1 as a template. In the event that the mutant-type gene was present, the extended strand (hereinafter referred to as "mutant-type extended strand") was formed using CTO-2 as a template. In the detection of the hybridization products between the extended strands and the SOs by a melting analysis, the two types of the extended strands can be differentially detected even using one type of the SO. For instance, where the extended strands are designed to have different sequences from each other on a portion to be hybridized with the SOs, the hybridization products have different T$_m$ values enabling to differentially detect the formation of extended strands.

The sequences of upstream primer, downstream primer, PTO, CTO and SO used in this Example are:

```
M677-F
                                        (SEQ ID NO: 7)
5'-GCAGGGAGCTTTGAGGCTGIIIIIAAGCACTTGA-3'

M677-R
                                        (SEQ ID NO: 8)
5'-CCTCACCTGGATGGGAAAGATIIIIIGGACGATGG-3'

M677-PTO-1
                                        (SEQ ID NO: 9)
5'-CCCAGGCAACCCTCCGATTTCATCATCACGCAGCTTTT
CTTTGAGGCT[Spacer C3]-3'

M677-PTO-2
                                        (SEQ ID NO: 10)
5'-CTCCTGCTCGCGTACTCCCGCAGACACCTTCTCCTTCA
AG[Spacer C3]-3'

M677-CTO-1
                                        (SEQ ID NO: 11)
5'-TCCGCTGCTTCACCACGCCTTCGAGAGGGTTGCCTGGG
[Spacer C3]-3'

M677-CTO-2
                                        (SEQ ID NO: 12)
5'-TCCGCTGCTTGACGACGCCTTCGATACGCGAGCAGGAG
[Spacer C3]-3'

M677-SO
                                        (SEQ ID NO: 13)
5'-[BHQ-2]TCCGCTGCTTCACCACGCCTTCGA
[CAL Red 610]-3'
(I: Deoxyinosine)
(Underlined letters indicate the 5'-tagging
portion of PTO)
(Bold letter indicates the sequence at C677T
mutation site of MTHFR gene)
```

The reaction was conducted in the final volume of 20 μl containing 30 ng of MTHFR (C677T) wild (C), hetero (C/T) or mutant (T) type human genomic DNA, 10 pmole of upstream primer (SEQ ID NO: 7), 10 pmole of downstream primer (SEQ ID NO: 8), each 5 pmole of PTOs (SEQ ID NO: 9 and 10), each 0.1 pmole of CTOs (SEQ ID NO: 11 and 12), 0.5 pmole SO (SEQ ID NO: 13) and 10 μl of 2× Master Mix containing 2.5 mM MgCl₂, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 40 cycles of 30 sec at 95° C., 60 sec at 55° C., and 30 sec at 72° C. After the reaction, melting curve was obtained by cooling the reaction mixture to 45° C., holding at 45° C. for 30 sec, and heating slowly at 45° C. to 85° C. The fluorescence was measured continuously during the temperature rise to monitor dissociation of an extended strand-SO hybrid. Melting peak was derived from the melting curve data.

As shown FIG. 12, a peak at 71.0° C. corresponding to the expected Tm value of the wild-type extended strand-SO hybrid was detected in the presence of the Wild-type template. A peak at 55.5° C. corresponding to the expected Tm value of the mutant-type extended strand-SO hybrid was detected in the presence of the mutant-type template. A peak at 71.0° C. (wild-type) and a peak at 55.5° C. (mutant-type) were detected in the presence of the hetero-type template. No peak was detected in the absence of any type of templates.

Example 4: Evaluation of PCE-SH Assay Using Upstream Oligonucleotide-Independent Cleavage of PTO PCE-SH assay was further evaluated for the detection of a target nucleic acid sequence without using upstream oligonucleotide in (i) real-time detection at a pre-determined temperature or (ii) melting analysis manner.

Taq DNA polymerase having a 5' nuclease activity was used for the cleavage of PTO, and the extension of PTO fragment.

PTO and CTO have no label. PTO and CTO are blocked with a carbon spacer at their 3'-ends. The synthetic oligonucleotide for *Neisseria gonorrhoeae* (NG) gene was used as a target template. SO has a fluorescent reporter molecule (CAL Fluor Red 610) at its 5'-end and has a quencher molecule (BHQ-2) at its 3'-end.

The sequences of synthetic template, PTO, CTO and SO used in this Example are:

NG-T
(SEQ ID NO: 1)
5'-AAATATGCGAAACACGCCAATGAGGGGCATGATGCTT

-continued
TCTTTTTGTTCTTGCTCGGCAGAGCGAGTGATACCGATCC
ATTGAAAAA-3'

NG-PTO
(SEQ ID NO: 3)
5'-<u>ACGACGGCTTGGCT</u>GCCCCTCATTGGCGTGTTTCG
[C3 spacer]-3'

NG-CTO
(SEQ ID NO: 4)
5'-GCGCTGGATACCCTGGACGATATGCAGCCAAGCCGTC
GT[C3 spacer]-3'

NG-SO-1
(SEQ ID NO: 5)
5'-[CAL Fluor Red 610]GCGCTGGATACCCTGGAC
GATATG[BHQ-2]-3'
(Underlined letters indicate the 5'-tagging portion of PTO)

4-1. Real-Time Detection at a Pre-Determined Temperature

The reaction was conducted in the final volume of 20 μl containing 2 pmole of synthetic template (SEQ ID NO: 1) for NG gene, 5 pmole of PTO (SEQ ID NO: 3), 0.5 pmole of CTO (SEQ ID NO: 4), 0.5 pmole of SO (SEQ ID NO: 5) and 10 μl of 2× Master Mix containing 2.5 mM MgCl₂, 200 μM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C., 60 sec at 60° C., and 30 sec at 72° C. Detection of the generated signal was performed at the hybridization step (60° C.) of each cycle. The detection temperature was determined to the extent that the extended strand-SO hybrid maintains a double-stranded form.

As shown FIG. 13A, the fluorescent signal was detected in the presence of the template. No signal was detected in the absence of the template.

4-2. Melting Analysis

After the reaction in Example 4-1, melting curve was obtained by cooling the reaction mixture to 55° C., holding at 55° C. for 30 sec, and heating slowly at 55° C. to 85° C. The fluorescence was measured continuously during the temperature rise to monitor dissociation of an extended strand-SO hybrid. Melting peak was derived from the melting curve data.

As shown FIG. 13B, a peak at 68.5° C. corresponding to the expected Tm value of the extended strand-SO hybrid was detected in the presence of template. No peak was detected in the absence of the template.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids by a PCE-SH (PTO Cleavage and Extension-Dependent Signaling Oligonucleotide Hybridization) assay in a liquid phase, comprising:
   (a) hybridizing the target nucleic acid sequence with an upstream oligonucleotide and a probing and targeting oligonucleotide (PTO); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence; the upstream oligonucleotide is located upstream of the PTO;
   (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;
   (c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;
   wherein the CTO is not labeled;
   (d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;
   (e) hybridizing the extended strand with a signaling oligonucleotide (SO); wherein the SO comprises a complementary sequence to the extended strand and at least one label; wherein the at least one label is located on the SO to provide a detectable signal directly by hybridization with the extended strand; and
   (f) detecting the signal in said liquid phase; wherein the CTO and SO are not immobilized on a solid substrate; whereby the detection of the signal indicates the presence of the extended strand and the presence of the target nucleic acid sequence; wherein the detectable signal is provided by (i) the label linked to the SO, (ii) a combination of the label linked to the SO and a label linked to the fragment from the PTO, (iii) a combination of the label linked to the SO and a label to be incorporated into the extended strand during the extension reaction of the step (d), or (iv) a combination of the label linked to the SO and an intercalating dye.

2. The method according to claim 1, wherein at least a portion of the SO comprises a complementary sequence to the extended sequence.

3. The method according to claim 1, wherein the SO is labeled with an interactive dual label comprising a reporter molecule and a quencher molecule and the hybridization between the SO and the extended strand in the step (e) induces change in signal from the interactive dual label to provide the detectable signal.

4. The method according to claim 1, wherein the SO is labeled with a single label and the hybridization between the SO and the extended strand in the step (e) induces change in signal from the single label to provide the detectable signal.

5. The method according to claim 1, wherein the method uses an additional SO comprising a complementary sequence to the extended strand, the two SOs are hybridized with the extended strand in an adjacent manner, the two SOs each comprises one label among a reporter molecule and a quencher molecule of an interactive dual label; and the hybridization between the two SOs and the extended strand induces change in signal from the interactive dual label to provide the detectable signal.

6. The method according to claim 1, wherein the SO comprises one label among a reporter molecule and a quencher molecule of an interactive dual label, the fragment from the PTO comprises the other label among the reporter molecule and the quencher molecule; the extended strand comprises the label originated from the fragment from the PTO, and wherein the hybridization between the SO and the extended strand induces change in signal from the interactive dual label to provide the detectable signal.

7. The method according to claim 1, wherein the SO comprises one label among a reporter molecule and a quencher molecule of an interactive dual label, and the templating portion of the CTO comprises a nucleotide having a first non-natural base; wherein the extension reaction in the step (d) is performed in the presence of a nucleotide having both a second non-natural base with a specific binding affinity to the first non-natural base and the other among the reporter molecule and the quencher molecule, thereby incorporating the label into the extended strand; wherein the hybridization between the SO and the extended strand induces change in signal from the interactive dual label to provide the detectable signal.

8. The method according to claim 1, wherein the SO comprises one label among a reporter molecule and a quencher molecule of an interactive dual label, and the extension reaction in the step (d) is performed in the presence of a nucleotide having the other among the reporter molecule and the quencher molecule, thereby incorporating the label into the extended strand; wherein the hybridization between the SO and the extended strand induces change in signal from the interactive dual label to provide the detectable signal.

9. The method according to claim 1, wherein the SO comprises an acceptor of a FRET (fluorescence resonance energy transfer) and the hybridization in the step (e) is preformed in the presence of an intercalating dye; wherein the hybridization between the SO and the extended strand induces change in signal from the acceptor of the SO to provide the detectable signal.

10. The method according to claim 1, wherein the PTO, CTO and/or SO is blocked at its 3'-end to prohibit its extension.

11. The method according to claim 1, wherein the upstream oligonucleotide is an upstream primer or an upstream probe.

12. The method according to claim 1, wherein the method further comprises the step of providing a detectable signal between the steps (e) and (f) by melting the hybridization resultant of the step (e) or by melting and hybridizing the hybridization resultant of the step (e); wherein the step (f) is performed by detecting the signal to determine the presence of the extended strand.

13. The method according to claim 1, wherein the method further comprises the step of providing and detecting a detectable signal after the step (f) by melting the hybridization resultant of the step (e) or by melting and hybridizing the hybridization resultant of the step (e), whereby the presence of the extended strand is determined one more time.

14. The method according to claim 13, wherein the presence of the extended strand is determined by a melting curve analysis or a hybridization curve analysis.

15. The method according to claim 1, wherein the method further comprises the step of denaturation between the steps (d) and (e).

16. The method according to claim 1, wherein the method further comprises repeating all or some of the steps (a)-(f) with denaturation between repeating cycles.

17. The method according to claim 16, wherein the method further comprises repeating the steps (a)-(e) with denaturation between repeating cycles, and melting the hybridization resultant of the step (e) or melting and hybridizing the hybridization resultant of the step (e) to provide a detectable signal; wherein the step (f) is performed by detecting the signal to determine the presence of the extended strand.

18. The method according to claim 1, wherein the steps (a)-(f) are performed in a reaction vessel or some of the steps (a)-(f) are performed in separate reaction vessels.

19. The method according to claim 1, wherein the method is performed to detect at least two types of target nucleic acid sequences; wherein the upstream oligonucleotide comprises at least two types of oligonucleotides, the PTO comprises at least two types of the PTOs, the CTO comprises at least two types of the CTOs and the SO comprises at least two types of the SOs.

20. The method according to claim 1, wherein the target nucleic acid sequence comprises a nucleotide variation.

21. The method according to claim 1, wherein the method is performed in the presence of a downstream primer.

22. A method for detecting a target nucleic acid sequence from a DNA or a mixture of nucleic acids by a PCE-SH (PTO Cleavage and Extension-Dependent Signaling Oligonucleotide Hybridization) assay in a liquid phase, comprising:
(a) hybridizing the target nucleic acid sequence with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequences; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;
(b) contacting the resultant of the step (a) to a template-dependent nucleic acid polymerase having a 5' nuclease activity under conditions for extension of the primers and for cleavage of the PTO; wherein when the PTO is hybridized with the target nucleic acid sequence, the upstream primer is extended and the extended strand induces cleavage of the PTO by the template-dependent nucleic acid polymerase having the 5' nuclease activity such that the cleavage releases a fragment comprising the 5'-tagging portion or a part of the 5'-tagging portion of the PTO;
(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;
wherein the CTO is not labeled;
(d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;
(e) hybridizing the extended strand with a signaling oligonucleotide (SO); wherein the SO comprises a complementary sequence to the extended strand and at least one label; wherein the at least one label is located on the SO to provide a detectable signal directly by hybridization with the extended strand; and
(f) detecting the signal in said liquid phase; wherein the CTO and SO are not immobilized on a solid substrate; whereby the detection of the signal indicates the presence of the extended strand and the presence of the target nucleic acid sequence; wherein the detectable signal is provided by (i) the label linked to the SO, (ii) a combination of the label linked to the SO and a label linked to the fragment from the PTO, (iii) a combination of the label linked to the SO and a label to be incorporated into the extended strand during the extension reaction of the step (d), or (iv) a combination of the label linked to the SO and an intercalating dye.

23. A method for detecting a target nucleic acid sequence from a DNA or a mixture of nucleic acids by a PCE-SH (PTO Cleavage and Extension-Dependent Signaling Oligonucleotide Hybridization) assay in a liquid phase, comprising:
(a) hybridizing the target nucleic acid sequence with a probing and targeting oligonucleotide (PTO); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO is cleaved by the enzyme having the 5' nuclease activity such that the cleavage releases a fragment comprising the 5'-tagging portion or a part of the 5'-tagging portion of the PTO;

(c) hybridizing the fragment released from the PTO with a capturing and templating oligonucleotide (CTO); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

wherein the CTO is not labeled;

(d) performing an extension reaction using the resultant of the step (c) and a template-dependent nucleic acid polymerase; wherein the fragment hybridized with the capturing portion of the CTO is extended to form an extended strand comprising an extended sequence complementary to the templating portion of the CTO, thereby forming an extended duplex;

(e) hybridizing the extended strand with a signaling oligonucleotide (SO); wherein the SO comprises a complementary sequence to the extended strand and at least one label; wherein the at least one label is located on the SO to provide a detectable signal directly by hybridization with the extended strand; and (f) detecting the signal in a liquid phase; wherein the CTO and SO are not immobilized on a solid substrate; whereby the detection of the signal indicates the presence of the extended strand and the presence of the target nucleic acid sequence;

wherein the detectable signal is provided by (i) the label linked to the SO, (ii) a combination of the label linked to the SO and a label linked to the fragment from the PTO, (iii) a combination of the label linked to the SO and a label to be incorporated into the extended strand during the extension reaction of the step (d), or (iv) a combination of the label linked to the SO and an intercalating dye.

* * * * *

SEQUENCE LISTING

<160> NUMBER OF SEQ ID NOS: 13

<210> SEQ ID NO 1
<211> LENGTH: 86
<212> TYPE: DNA
<213> ORGANISM: Artificial Sequence
<220> FEATURE:
<223> OTHER INFORMATION: NG-T

```
<400> SEQUENCE: 1
aaatatgcga aacacgccaa tgagggggcat gatgctttct ttttgttctt gctcggcaga        60
gcgagtgata ccgatccatt gaaaaa                                              86

<210> SEQ ID NO 2
<211> LENGTH: 21
<212> TYPE: DNA
<213> ORGANISM: Artificial Sequence
<220> FEATURE:
<223> OTHER INFORMATION: NG-R

<400> SEQUENCE: 2
caatggatcg gtatcactcg c                                                   21

<210> SEQ ID NO 3
<211> LENGTH: 35
<212> TYPE: DNA
<213> ORGANISM: Artificial Sequence
<220> FEATURE:
<223> OTHER INFORMATION: NG-PTO

<400> SEQUENCE: 3
acgacggctt ggctgcccct cattggcgtg tttcg                                    35

<210> SEQ ID NO 4
<211> LENGTH: 39
<212> TYPE: DNA
<213> ORGANISM: Artificial Sequence
<220> FEATURE:
<223> OTHER INFORMATION: NG-CTO

<400> SEQUENCE: 4
gcgctggata ccctggacga tatgcagcca agccgtcgt                                39

<210> SEQ ID NO 5
<211> LENGTH: 24
<212> TYPE: DNA
<213> ORGANISM: Artificial Sequence
<220> FEATURE:
<223> OTHER INFORMATION: NG-SO-1

<400> SEQUENCE: 5
gcgctggata ccctggacga tatg                                                24

<210> SEQ ID NO 6
<211> LENGTH: 21
<212> TYPE: DNA
<213> ORGANISM: Artificial Sequence
<220> FEATURE:
<223> OTHER INFORMATION: NG-F

<400> SEQUENCE: 6
tacgcctgct actttcacgc t                                                   21

<210> SEQ ID NO 7
<211> LENGTH: 34
<212> TYPE: DNA
<213> ORGANISM: Artificial Sequence
<220> FEATURE:
<223> OTHER INFORMATION: M677-F
<220> FEATURE:
<221> NAME/KEY: misc_feature
<222> LOCATION: (20)..(24)
<223> OTHER INFORMATION: n denotes deoxyinosine

<400> SEQUENCE: 7
```

```
gcagggagct tgaggctgn nnnnaagcac ttga                                    34
```

<210> SEQ ID NO 8
<211> LENGTH: 35
<212> TYPE: DNA
<213> ORGANISM: Artificial Sequence
<220> FEATURE:
<223> OTHER INFORMATION: M677-R
<220> FEATURE:
<221> NAME/KEY: misc_feature
<222> LOCATION: (22)..(26)
<223> OTHER INFORMATION: n denotes deoxyinosine

<400> SEQUENCE: 8

```
cctcacctgg atgggaaaga tnnnnnggac gatgg                                  35
```

<210> SEQ ID NO 9
<211> LENGTH: 48
<212> TYPE: DNA
<213> ORGANISM: Artificial Sequence
<220> FEATURE:
<223> OTHER INFORMATION: M677-PTO-1

<400> SEQUENCE: 9

```
cccaggcaac cctccgattt catcatcacg cagcttttct ttgaggct                    48
```

<210> SEQ ID NO 10
<211> LENGTH: 40
<212> TYPE: DNA
<213> ORGANISM: Artificial Sequence
<220> FEATURE:
<223> OTHER INFORMATION: M677-PTO-2

<400> SEQUENCE: 10

```
ctcctgctcg cgtactcccg cagacacctt ctccttcaag                             40
```

<210> SEQ ID NO 11
<211> LENGTH: 38
<212> TYPE: DNA
<213> ORGANISM: Artificial Sequence
<220> FEATURE:
<223> OTHER INFORMATION: M677-CTO-1

<400> SEQUENCE: 11

```
tccgctgctt caccacgcct tcgagagggt tgcctggg                               38
```

<210> SEQ ID NO 12
<211> LENGTH: 38
<212> TYPE: DNA
<213> ORGANISM: Artificial Sequence
<220> FEATURE:
<223> OTHER INFORMATION: M677-CTO-2

<400> SEQUENCE: 12

```
tccgctgctt gacgacgcct tcgatacgcg agcaggag                               38
```

<210> SEQ ID NO 13
<211> LENGTH: 24
<212> TYPE: DNA
<213> ORGANISM: Artificial Sequence
<220> FEATURE:
<223> OTHER INFORMATION: M677-SO

<400> SEQUENCE: 13

```
tccgctgctt caccacgcct tcga                                              24
```